(12) United States Patent
Sunkara et al.

(10) Patent No.: US 9,522,201 B2
(45) Date of Patent: Dec. 20, 2016

(54) METHOD AND APPARATUS FOR THE DISINFECTION OR STERILIZATION OF MEDICAL APPAREL AND ACCESSORIES

(71) Applicant: NOSOCOM SOLUTIONS, INC., Emeryville, CA (US)

(72) Inventors: Naresh Sunkara, Emeryville, CA (US); Ricardo R Garcia, Albany, CA (US); Nikhil Santosh Naikal, New York, NY (US); Jaya Sunkara, Emeryville, CA (US)

(73) Assignee: NOSOCOM SOLUTIONS, INC., Emeryville, CA (US)

(*) Notice: Subject to any disclaimer, the term of this patent is extended or adjusted under 35 U.S.C. 154(b) by 0 days.

(21) Appl. No.: 14/859,113

(22) Filed: Sep. 18, 2015

(65) Prior Publication Data

US 2016/0008499 A1 Jan. 14, 2016

Related U.S. Application Data

(60) Division of application No. 14/561,050, filed on Dec. 4, 2014, now Pat. No. 9,162,001, which is a continuation of application No. PCT/US2014/043442, filed on Jun. 20, 2014.

(60) Provisional application No. 61/837,611, filed on Jun. 20, 2013.

(51) Int. Cl.
*A61L 2/00* (2006.01)
*A61B 1/00* (2006.01)
(Continued)

(52) U.S. Cl.
CPC .............. *A61L 2/10* (2013.01); *A61B 90/98* (2016.02); *A61L 2/24* (2013.01); *A61L 2202/14* (2013.01); *A61L 2202/24* (2013.01)

(58) Field of Classification Search
CPC ................................. A61L 2/19; D06F 93/00
(Continued)

(56) References Cited

U.S. PATENT DOCUMENTS 2,612,994 A 10/1952 Woodland et al.
5,882,589 A 3/1999 Mariotti
(Continued)

OTHER PUBLICATIONS

Allegranzi B. et al., "Burden of endemic health-care-associated infection in developing countries: systematic review and meta-analysis," Lancet 377(9761):228-241, 2011.
(Continued)

*Primary Examiner* — Monzer R Chorbaji
(74) *Attorney, Agent, or Firm* — Kilpatrick Townsend & Stockton LLP

(57) ABSTRACT

The present invention provides an apparatus for disinfecting and/or sterilizing medical or laboratory apparel or accessories, comprising: a cabinet, a disinfecting system housed within the cabinet, wherein the disinfecting system comprises at least one disinfecting agent, and an embedded computer or a programmable logic controller (PLC) housed within the cabinet, wherein the embedded computer or the PLC controls one or more systems of the apparatus. The cabinet has advanced tracking features (e.g., RFID readers) that can track the apparel or accessories being disinfected. The embedded computer or PLC has the capabilities to send electronic messages to users or additional computers for further transmission of information at regular intervals. Methods for disinfecting and/or sterilizing medical or laboratory apparel or accessories are also provided.

18 Claims, 8 Drawing Sheets

(51) Int. Cl.
  G01N 23/00    (2006.01)
  A61L 2/10     (2006.01)
  A61L 2/24     (2006.01)
(58) Field of Classification Search
  USPC ... 422/22–23, 28, 1; 134/1, 6, 8, 22.1, 56 R;
                          600/133, 198; 250/455.11, 492.1;
                                                    73/86.01
  See application file for complete search history.

(56)                References Cited

U.S. PATENT DOCUMENTS 7,507,369  B2 *   3/2009   Lu .......................... A61L 2/04
                                                                219/679
  7,608,228  B2    10/2009   Horacek, Jr. et al.
  9,162,001  B2    10/2015   Sunkara et al.
  2006/0283483 A1  12/2006   Pieroni et al.
  2009/0194468 A1 * 8/2009   Santicchi ................ D06F 93/00
                                                                209/576
  2013/0137162 A1   5/2013   Larson et al.

OTHER PUBLICATIONS

Allegranzi, B. et al., "Report on the burden of endemic healtcare-associated infection worldwide," World Health Organization, 20 Avenue Appia, CH-1211 Geneva 27, Switzerland, 40 pages, 2011.
Barrie, D., "Infection-control in practice. How hospital linen and laundry services are provided," Journal of Hospital Infection, 27(3):219-235, 1994.
Becker, M. and Wang, Z. "Origin of ultraviolet damage in DNA," J. Mol. Biol., 210(3):429-438, 1989.
Burden M. et al., "Newly cleaned physician uniforms and infrequently washed white coats have similar rates of bacterial contamination after an 8-hour workday: a randomized controlled trial," J. Hosp. Med., 6(4):177-182, 2011.
Burwen, D. et al., "Invasive aspergillosis outbreak on a hematology-oncology ward," Infection control and hospital epidemiology, 22(1):45-48, 2001.
Cardullo, M., "Genesis of the versatile RFID tag," RFID Journal, Apr. 21, 2003, 3 pages.
Centers for Disease Control and Prevention, "Healthcare-associated Infections (HAI), Prevention," 2010, retrieved online at <http://www.cdc.gov/hai/> on Oct. 8, 2014, 2 pages.
Centers for Disease Control and Prevention, "Winnable Battles—Healthcare-associated infections," retrieved online at <http://www.cdc.gov/winnablebattles/healthcareassociatedinfections/index.html> on Oct. 8, 2014, 2 pages.
Conner-Kerr, T. et al., "The effects of ultraviolet radiation on antibiotic-resistant bacteria in vitro," Ostomy/Wund Management, 44(10):50-56, 1998.
Davies, A. et al., "Gaseous and air decontamination technologies for Clostridium difficile in the healthcare environment," J. Hosp. Infect., 77(3):199-203, 2011.
Denning, D., "Invasive aspergillosis," Clin. Infect. Dis., 26(4):781-803, 1998.
Frieden, T., "Maximizing infection prevention in the next decade: Defining the unacceptable," Infection Control and Hospital Epidemiology, 31(S1):S1-S3, 2010.
Gaspard, P. et al., "Meticillin-resistant Staphylococcus aureus contamination of healthcare workers' uniforms in long-term care facilities," J. Hosp. Infect., 71(2):170-175, 2009.
Hambraeus, A. & Ransjo, U., "Attempts to control clothes-borne infection in a burn unit. I. Experimental investigations of some clothes for barrier nursing," J. Hyg., Camb., 79(2):193-202, 1977.
Hambraeus, A. and Laurell, G., "Infections in a burns unit. An attempt to study the airborne transfer of bacteria," Contributions to Microbiology and Immunology 1:459-468, 1973.
Hambraeus, A. "Dispersal and transfer of Staphylococcus aureus in an isolation ward for burned patients," J. Hyg., Camb., 71(4):787-797, 1973.
Hambraeus, A., "Transfer of Staphylococcus aureus via nurses' uniforms," J. Hyg., Camb., 71(4):799-814, 1973.
Hijnen, W. et al., "Inactivation credit of UV radiation for viruses, bacteria and protozoan (oo)cysts in water: a review," Water Research, 40(1):3-22, 2006.
Kallen, J. et al., "Vital Signs: Carbapenem-resistant enterobacteriaceae," Morbidity and Mortality Weekly Report, Centers for Disease Control and Prevention, 62(9):165-170, 2013.
Kao, A. et al., "The epidemiology of candidemia in two United States cities: Results of a population-based based active surveillance," Clin. Infect. Dis., 29(5):1164-1170, 1999.
Klein, B. et al., "Reduction of nosocomial infection during pediatric intensive care by protective isolation," N. Engl. J. Med., 320(26):1714-1721, 1989.
Kridner, J., "Beagleboard.org.—community supported open hardware computers for making," BeagleBoard.org Foundation, 1380 Presidential Dr., Ste. 100, Richardson, TX 75081-2437, 2013, retrieved online at <http://beagleboard.org/> on Oct. 8, 2014, 3 pages.
Lidwell, O. et al., "Transfer of micro-organisms between nurses and patients in a clean air environment," J. Appl. Bact., 37(4):649-656, 1974.
Loh, W. et al., "Bacterial flora on the white coats of medical students," J. Hosp. Infect., 45(1):65-68, 2000.
Moore, G. et al., "Use of UV-C radiation to disinfect non-critical patient care items: a laboratory assessment of the Nanoclave Cabinet," BMC Infect. Dis., 12:174, 2012.
Munoz-Price, L. et al., "Associations between bacterial contamination of health care workers' hands and contamination of white coats and scrubs," American Journal of Infection Control, 40(9):E245-E248, 2012.
Nerandzic, M. et al., "Evaluation of an automated ultraviolet radiation device for decontamination of Clostridium difficile and other healthcare-associated pathogens in hospital rooms," BMC Infect. Dis., 10:197, 2010.
Nordstrom, J. et al., "Comparison of bacteria on new, disposable, laundered, and unlaundered hospital scrubs," American Journal of Infection Control, 40(6):539-543, 2012.
Nystrom, B., "The contamination of gowns in an intensive care unit," J. Hosp. Infect. 2(2):167-170, 1981.
Office of Disease Prevention and Health Promotion, "health.gov (/). National action plan to prevent healthcare-associated infections: Road map to elimination," 2012, retrieved online at <http://www.health.gov/hai/prevent_hai.asp> on Oct. 8, 2014, 4 pages.
Palazzo, S. and Hocken, D., "Patients' perspectives on how doctors dress," J. Hosp. Infect., 74(1):30-34, 2010.
Peleg, A. and Hooper, D., "Hospital-acquired infections due to gram-negative bacteria," N. Engl. J. Med., 362(19):1804-1813, 2010.
Perfect, J. and Schell, W., "The new fungal opportunists are coming," Clin. Infect. Dis., 22:S112-S118, 1996.
Perry, C. et al., "Bacterial contamination of uniforms," J. Hosp. Infect., 48(3):238-241, 2001.
Pigeot-Remy, S. et al., "Bactericidal efficiency and mode of action: A comparative study of photochemistry and photocatalysis," Water Research, 46(10):3208-3218, 2012.
Pilonetto, M. et al., "Hospital gowns as a vehicle for bacterial dissemination in an intensive care unit," Brazilian Journal of Infectious Diseases, 8(3):206-210, 2004.
Ransjo, U., "Attempts to control clothes-borne infection in a burn unit, 3. An open-roofed plastic isolator or plastic aprons to prevent contact transfer of bacteria," J. Hyg., Camb., 82(3):385-395, 1979.
Ransjo, U., "Attempts to control clothes-borne infection in a burn unit, 2. Clothing routines in clinical use and the epidemiology of cross-colonization," J. Hyg., Camb., 82(3):369-384, 1979.
Saloojee, H. and Steenhoff, A., "The health professional's role in preventing nosocomial infections," Postgraduate Medical Journal, 77(903):16-19, 2001.
Scott, R., "The direct medical costs of healthcare-associated infections in U.S. hospitals and the benefits of prevention," Division of

(56) References Cited

OTHER PUBLICATIONS

Healthcare Quality Promotion, National Center for Preparedness, Detection, and Control of Infectous Diseases, Coordinating Center for Infectous Diseases, Centers for Disease Control and Prevention, Mar. 2009, 16 pages.

Sehulster, L. et al., "Guidelines for environmental infection control in health-care facilities," U.S. Department of Health and Human Services, Centers for Disease Control and Prevention, Atlanta, 2003, retrieved online at <http://www.cdc.gov/mmwr/preview/mmwrhtml/rr5210a1.htm> on Oct. 8, 2014, 62 pages.

Solomon, S. et al., "Nosocomial fungemia in neonates associated with intravascular pressure-monitoring devices," Pediatr. Infect. Dis., 5(6):680-685, 1986.

Speers, R., Jr. et al., "Contamination of nurses' uniforms with *Staphylococcus aureus*," Lancet 2(7614):233-235, 1969.

Treakle, A. et al., "Bacterial contamination of health care workers' white coats," American Journal of Infection Control, 37(2):101-105, 2009.

Uneke, C. and Ijeoma, P., "The potential for nosocomial infection transmission by white coats used by physicians in Nigeria: implications for improved patient-safety initiatives," World Health & Population, 11(3):44-54, 2010.

United States Environmental Protection Agency, "Pesticides: science and policy—laundry additives—residual self-sanitation, DIS/TSS-14 Jul. 29, 1981" retrieved online at <http://www.epa.gov/oppad001/dis_tss_docs/dis-14.htm> on Oct. 8, 2014, 2 pages.

Van Der Weyden, M., "White coats and the medical profession: Time to rediscover the symbol of our purpose and our pride?" Medical Journal of Australia, 174:324-325, 2001.

Wiener-Well, Y. et al., "Nursing and physician attire as possible source of nosocomial infections," American Journal of Infection Control, 39(7):555-559, 2011.

\* cited by examiner

300

310

METHOD AND APPARATUS FOR THE DISINFECTION OR STERILIZATION OF MEDICAL APPAREL AND ACCESSORIES

CROSS-REFERENCES TO RELATED APPLICATIONS

The present application is a divisional of U.S. application Ser. No. 14/561,050, filed Dec. 4, 2014, which application is a continuation of PCT/US14/43442, filed Jun. 20, 2014, which application claims priority to U.S. Provisional Application No. 61/837,611, filed Jun. 20, 2013, the disclosures of which are hereby incorporated by reference in their entirety for all purposes.

FIELD OF THE INVENTION

This invention relates generally to disinfection systems and apparatuses, and more particularly to methods and apparatuses for the disinfection or sterilization of medical and laboratory apparel and accessories.

BACKGROUND OF THE INVENTION

Healthcare acquired infections are defined by the Center for Disease Control and Prevention (CDC) as infections acquired by patients while receiving treatment for another condition in a health care setting. These infections are caused by a variety of bacteria, viruses, fungi, and other pathogens that primarily affect immunocompromised and elderly people, especially if the causative organism has developed resistance to a number of antimicrobial agents (3, 31-35). Healthcare acquired infections account for about 100,000 deaths and anywhere from $28.4-45 billion a year in medical-related expenses in the United States, and it is estimated that hundreds of millions of patients around the world are affected by health acquired infections each year (1). Although these infections are costly and deadly, they are preventable and efforts to maximize the efficiency of prevention efforts across the United States are being coordinated by the U.S. Department of Health and Human Services (2, 36, 37).

Transmission of healthcare acquired infections is most commonly associated with invasive medical devices or surgical procedures that result in central line-associated bloodstream infections, catheter-associated urinary tract infections, and ventilator-associated pneumonia (3). However, healthcare acquired infections (HAI) are also transmitted by contaminated uniforms, scrubs, and coats worn by health care workers, such as physicians and nurses. Despite their best intentions, health care workers unknowingly act as vectors to various bacteria and pathogens that come into contact with their apparel, causing cross-contamination and the spread of healthcare acquired infections in patients (21). Studies have implicated the coats of health care workers for being contaminated with bacteria responsible for the development of healthcare acquired infections (4-24). This includes bacteria like methicillin-resistant *Staphylococcus aureus* (MRSA), *Clostridium difficile*, vancomycin-resistant enterococcus (VRE), carbapenem-resistant enterococcus (CRE), etc. (4-24).

One of the main reasons for this problem is that the coats and other apparel worn by health care workers are not laundered as often or as effectively as they should be (7). The current procedure used by hospitals to clean white coats and/or uniforms is to launder them either on-site or off-site using laundry facilities, following the regulations proposed by the CDC (38). However, laundering coats and other healthcare worker apparel on a daily basis places an inefficient and expensive burden on hospitals. In a cost-saving effort, hospitals commonly allow health care workers to launder their own uniforms, white coats and even operating room scrubs at home (26). However, domestic laundering practices differ greatly from industrial laundering practices (40, 41). As a result, this cost-saving effort has been shown to lead to the contamination of home laundered uniforms with one or more pathogens before the start of a healthcare worker's shift (42). In one study, scrub contamination of at least one of the test organisms increased to 54% at the end of shifts. Also, VRE was found on 31% of uniforms, *C. difficile* on 19%, and MRSA on 15% (42). Similarly, another study isolated pathogens from 48% of hospital gowns (43). A significant increase in total bacteria from the beginning to the end of a work shift was found, with average counts increasing from 2.2 $CFU/cm^2$ to 4.9 $CFU/cm^2$ (43).

Even though some hospitals provide excellent laundering facilities, health care workers tend to not use these services regularly. A recent study at the University of Maryland reported that about 65% of the health care workers washed their coats less than once a week and 15% less than once a month (21). Implementation of effective laundering practices is often hindered by a lack of support from administrators and poor compliance by doctors, nurses, and other health care workers. Some health professionals believe that their apparel is clean and sterile when it is not. Many are visibly upset when their poor hygiene practices are exposed and are offended when it is suggested that they may be potential vectors of disease and are spreading virulent microorganisms among their patients (44).

Further, as laundering of apparel is the primary procedure followed in healthcare settings for disinfection, the ability to provide quick disinfection of coats, uniforms, scrubs, and other objects and apparel used in the healthcare environment suffers from a lack of available technology. Due to the concerns arising from the spread of healthcare acquired infections by apparel worn by healthcare workers, the United Kingdom's Department of Health recently recommended that hospitals adopt a "bare below the elbows" dress code and that white coats be disallowed in an attempt to decrease the transmission of bacteria (20, 39). This recommendation reflects the seriousness of this problem but does not adequately address the spread of infection by contaminated apparel. While bare below the arms policy reduces the spread of pathogens by the sleeves, the unhygienic habit of not washing health care apparel on a daily basis still spreads diseases. Thus, there remains a need for a viable source of disinfection in healthcare facilities that will complement the existing efforts to reduce healthcare acquired infections. The present invention fulfills this need as well as other needs.

BRIEF SUMMARY OF THE INVENTION

The present invention relates to a method and an apparatus for disinfecting and/or sterilizing medical or laboratory apparel and/or accessories. In one aspect, an apparatus for disinfecting and/or sterilizing medical or laboratory apparel and/or accessories is provided. In one embodiment, the apparatus comprises:
 (a) a cabinet capable of housing one or more items of medical or laboratory apparel and/or accessories;
 (b) a disinfecting system housed within the cabinet, wherein the disinfecting system comprises at least one disinfecting agent; and (c) an embedded computer or a programmable logic controller (PLC) housed within the cabinet.

In some embodiments, the embedded computer or PLC controls the disinfecting system. In some embodiments, the embedded computer or PLC controls one or more (e.g., all) systems of the apparatus. In some embodiments, the embedded computer or PLC controls one or more (e.g., all) of the following systems: a disinfecting system, a scanning system, a horizontal linear sub-system, a vertical linear sub-system, a garment identification system, a hanging system, a hanger state measurement system, a human machine interface, a lighting system, a locking system, a calibration system, and a ranging system. In some embodiments, the embedded computer or PLC controls 1, 2, 3, 4, 5, 6, 7, 8, 9, 10, 11, 12, or more systems.

In some embodiments, the disinfecting agent is a source of ultraviolet (UV) radiation, a source of infrared light, or a chemical. In some embodiments, the disinfecting agent is a UV mercury vapor lamp, a UV light-emitting diode (LED), a pulsed UV light, a UV deuterium lamp, a UV metal halide lamp, or any other UV light emitting source such as a UV-C light source. In some embodiments, the disinfecting system comprises at least one source of ultraviolet (UV) radiation and a chemical disinfectant. In some embodiments, a single or multiple disinfecting systems or disinfecting agents are mounted within the apparatus. In some embodiments, a single or multiple disinfecting systems or disinfecting agents are mounted within the apparatus in a stationary position. In some embodiments, the disinfecting agent is exposed to the one or more items of medical or laboratory apparel and/or accessories for a time period of about 30 seconds to about 30 minutes.

In some embodiments, the apparatus comprises a scanning system (a mechanical system that allows the UV light to move around the apparel) housed within the cabinet, the scanning system comprising a slide and a carriage mounted on the slide. In some embodiments, the disinfecting system is mounted on the carriage. In some embodiments, the carriage moves horizontally, vertically, both horizontally and vertically, or circularly. In some embodiments, the carriage moves along specified coordinates such as the X axis, Y axis, and/or Z axis. In some embodiments, the carriage moves along an XY axis, a YZ axis, and/or an XZ axis. In some embodiments, the carriage moves along an XYZ axis. In particular embodiments, the X, Y, and Z axes correspond to the axes in a three-dimensional Cartesian coordinate system.

In some embodiments, the apparatus is used for disinfecting or sterilizing one or more items of medical or laboratory apparel, such as coats (e.g., white coats or lab coats), scrubs, uniforms, aprons, shoes, and/or accessories (e.g., shoes, socks, ties, hosiery, watches, headbands, scrub caps, stethoscopes, mobile phones, note pads, writing equipment like pens, and pressure cuffs). The apparatus is capable of disinfecting or sterilizing both apparel and accessories separately or together. In some embodiments, the apparatus is used for disinfecting and/or sterilizing 1, 2, 3, 4, 5, 6, 7, 8, 9, 10, 15, 20, 25, 30, 35, 40, 45, 50, or more items of medical or laboratory apparel and/or accessories.

In some embodiments, the apparatus further comprises a hanger system housed within the interior of the cabinet, wherein the hanger system comprises one or more hangers configured in either fixed positions or dynamic positions. The hangers may be loaded with apparel and/or accessories separately or together.

In some embodiments, the apparatus further comprises a system for identifying and tracking items of medical or laboratory apparel and/or accessories, hereinafter referred to as a garment identification or tracking system. In some embodiments, the garment identification or tracking system comprises a sensor that is used in conjunction with identification tags for the one or more items of medical or laboratory apparel and/or accessories (e.g., a sensor or scanner that reads an identification tag attached to an item of medical or laboratory apparel or accessory). In some embodiments, the garment identification or tracking system comprises a radio-frequency identification (RFID) reader mounted on the carriage or at a suitable location in or on the cabinet and an RFID tag for each of the one or more items of medical or laboratory apparel and/or accessories. In some embodiments, the RFID tag is attached to the item of medical or laboratory apparel and/or accessory. In some embodiments, the garment identification or tracking system comprises a barcode reader mounted on the carriage or at a suitable location in or on the cabinet and a barcode tag for each of the one or more items of medical or laboratory apparel and/or accessories. In some embodiments, the garment identification or tracking system comprises one or more identification tags that are used in conjunction with a sensor in a mobile device. For example, the embedded computer or PLC receives data from a tag associated with an article of apparel and communicates an electronic message to a user's mobile device via a sensor in the mobile device. This message may include, for example, a reminder to disinfect the user's lab coat at the end of every 8 hour workday. In particular embodiments, a tracking system (e.g., an RFID reader, barcode reader, etc.) is housed in the cabinet and is configured to communicate with a device (e.g., an RFID tag, barcode tag, etc.) located on an item of apparel or accessory to enable the apparatus to transmit electronic messages to a user (e.g., reminders to disinfect an item at pre-determined intervals). In certain preferred embodiments, the garment identification or tracking system is capable of capturing disinfection status information on each item of medical or laboratory apparel and/or accessory and processing the data for usage analysis or for providing status updates to users.

In some embodiments, the apparatus further comprises a display screen mounted to the exterior of the cabinet. In some embodiments, the display screen comprises a Human Machine Interface (HMI) through which a user can unlock the apparatus, determine the status of a disinfection cycle or disinfection status of an item of apparel or accessory, and/or determine the location within the apparatus of an item of medical or laboratory apparel and/or accessory associated with the user.

In some embodiments, the apparatus further comprises a locking system. The locking system ensures that the interior of the cabinet cannot be accessed without proper credentials and prevents user exposure to UV illumination or other disinfecting agents. In some embodiments, the locking system functions to keep users secure from the UV or other disinfection agents that are used in the apparatus.

In some embodiments, one or more interior surfaces of the cabinet are coated with a reflective material or other means to facilitate reflection of UV light to maximize exposure to the medical or laboratory apparel and/or accessories. In some embodiments, the interior surface functions to reduce the exposure of the surrounding environment to the disinfecting agent.

In particular embodiments, the apparatus comprises:
(a) a cabinet capable of housing one or more items of medical or laboratory apparel and/or accessories;

(b) a disinfecting system housed within the cabinet, wherein the disinfecting system comprises at least one disinfecting agent;
(c) an embedded computer or a programmable logic controller (PLC) housed within the cabinet; and
(d) a garment identification or tracking system, wherein the garment identification or tracking system captures disinfection status information on each of the one or more items of medical or laboratory apparel and/or accessories and processes the information (e.g., data) for usage analysis and/or for providing one or more status updates to one or more users.

In another aspect, a method for disinfecting and/or sterilizing medical or laboratory apparel and/or accessories is provided. In some embodiments, the method comprises:
(a) placing one or more items of medical or laboratory apparel and/or accessories in an apparatus comprising (i) a cabinet; (ii) a disinfecting system housed within the cabinet, wherein the disinfecting system comprises at least one disinfecting agent; and (iii) an embedded computer or a programmable logic controller (PLC) housed within the cabinet; and
(b) exposing the one or more items of medical or laboratory apparel and/or accessories to the at least one disinfecting agent under conditions suitable for inactivating or killing pathogens, thereby disinfecting or sterilizing the one or more items of medical or laboratory apparel and/or accessories.

In some embodiments, the disinfecting agent is a source of ultraviolet (UV) radiation, a source of infrared light, or a chemical. In some embodiments, the method comprises exposing the one or more items of medical or laboratory apparel and/or accessories to one or more disinfection cycles.

In certain embodiments, the apparatus used in the methods of the present invention for disinfecting and/or sterilizing medical or laboratory apparel and/or accessories further comprises one or more (e.g., 1, 2, 3, 4, 5, 6, 7, 8, 9, 10, or all) of the following systems: a garment identification or tracking system, a scanning system, a horizontal linear sub-system, a vertical linear sub-system, a hanging system, a hanger state measurement system, a human machine interface, a lighting system, a locking system, a calibration system, and a ranging system.

In particular embodiments, the method comprises:
(a) placing one or more items of medical or laboratory apparel and/or accessories in an apparatus comprising (i) a cabinet; (ii) a disinfecting system housed within the cabinet, wherein the disinfecting system comprises at least one disinfecting agent; (iii) an embedded computer or a programmable logic controller (PLC) housed within the cabinet; and (iv) a garment identification or tracking system, wherein the garment identification or tracking system captures disinfection status information on each of the one or more items of medical or laboratory apparel and/or accessories and processes the information (e.g., data) for usage analysis and/or for providing one or more status updates to one or more users; and
(b) exposing the one or more items of medical or laboratory apparel and/or accessories to the at least one disinfecting agent under conditions suitable for inactivating or killing pathogens, thereby disinfecting or sterilizing the one or more items of medical or laboratory apparel and/or accessories.

Other objects, features, and advantages of the present invention will be apparent to one of skill in the art from the following detailed description and figures.

Figure 1A:
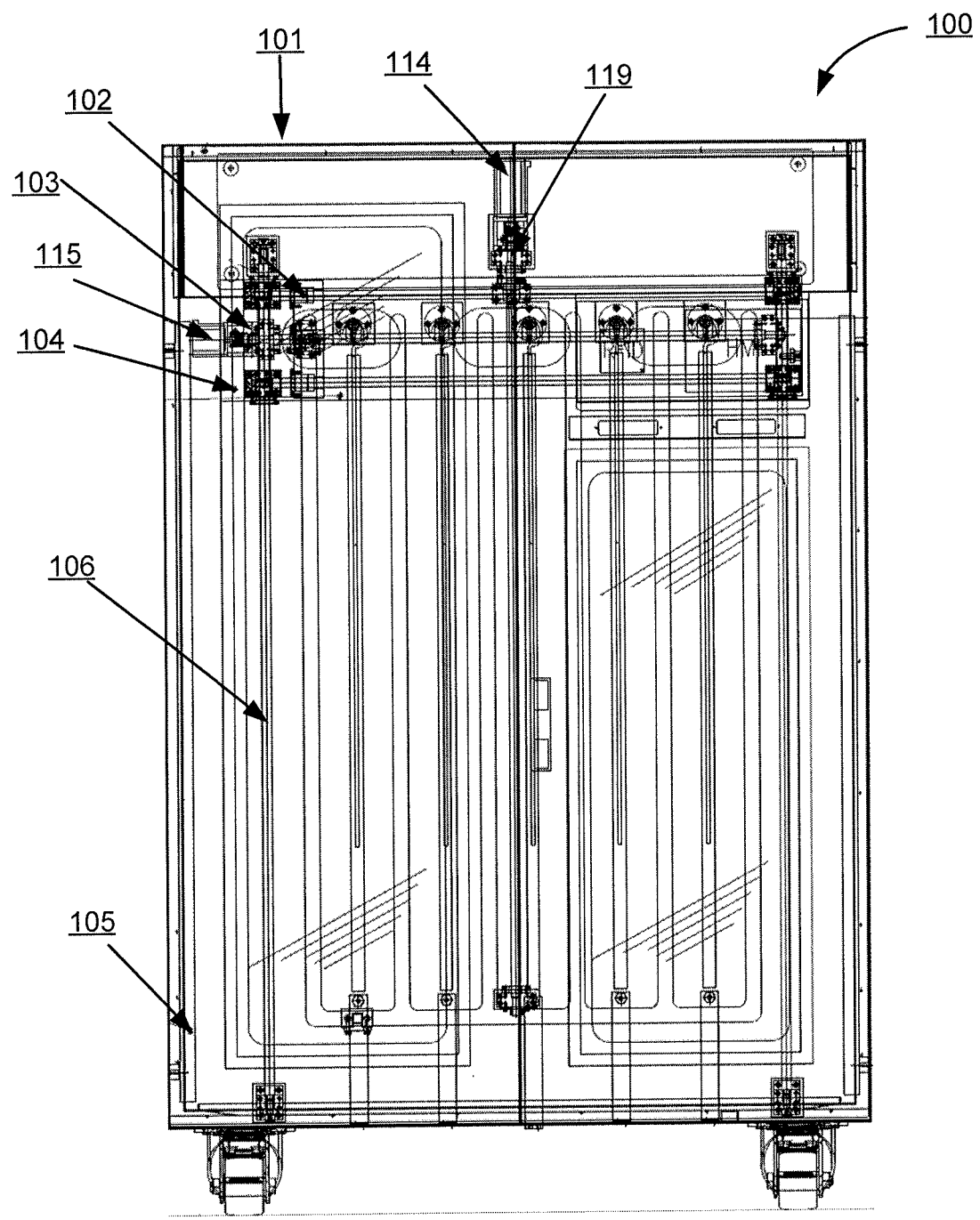
FIG. 1A illustrates the front view of an exemplary disinfection cabinet with a UV scanning device in accordance with an embodiment of the invention.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

I. Introduction

The present invention is based, in part, on the well-documented bactericidal effects of ultraviolet radiation such as, for example, UV-C radiation in the region of approximately 200-280 nm that result in inactivation of microbial DNA. A primary benefit of using UV light for disinfection is that it does not contain or create any residuals or byproducts, such as can occur with chemical methods of purification. Different species of microorganisms require varying levels of UV-C exposure, but nearly all can be effectively inactivated with a fluence level of about 30 mJ/cm$^2$ of surface area. Fluence levels of this intensity can achieve a 4-log reduction for most microorganisms, equivalent to a 99.99% reduction in the number of active organisms. The effectiveness of UV-C disinfection is dependent on line of sight exposure of the microorganisms to the UV source. Other factors that contribute to the effectiveness of UV-C disinfection include the intensity of UV light, including the length of time a microorganism is exposed to UV; the distance of the surface from the radiation source; the presence of dust and dirt on the lamp surface; the presence of particles that can protect the microorganisms from UV; and a microorganism's ability to withstand UV during its exposure. The present invention satisfies these needs and provides related advantages as well.

II. Apparatuses for Disinfecting and/or Sterilizing Medical or Laboratory Apparel In one aspect, the present invention provides apparatuses for disinfecting or sterilizing one or more items of medical or laboratory apparel and/or accessories. In some embodiments, the apparatus comprises:

(a) a cabinet capable of housing one or more items of medical or laboratory apparel and/or accessories;

(b) a disinfecting system housed within the cabinet, wherein the disinfecting system comprises at least one disinfecting agent; and (c) an embedded computer or a programmable logic controller (PLC) housed within the cabinet.

In some embodiments, the apparatus further comprises a scanning system housed within the cabinet. The scanning system is a mechanical system, comprising a slide and a carriage mounted on the slide that facilitates movement of the UV light or other disinfecting agent around the apparel and/or accessory. In some embodiments, the carriage carries the disinfecting system.

In some embodiments, the apparatus further comprises one or more of the following: a garment identification system; a hanging system comprising one or more hangers configured in either fixed positions or dynamic positions; a hanger state measurement system; one or more hanger indicators; a device to enable authorized access to the inside of the cabinet; a display screen and/or touch screen; a light source indicator for detecting the status of a light source; a calibration system; a ranging system; and an internal storage box.

In some embodiments, the embedded computer or PLC controls the disinfecting system. In some embodiments, the embedded computer or PLC controls one or more (e.g., all) systems of the apparatus. In some embodiments, the embedded computer or PLC controls one or more (e.g., all) of the following systems: a disinfecting system, a scanning system, a horizontal linear sub-system, a vertical linear sub-system, a garment identification system, a hanging system, a hanger state measurement system, a human machine interface, a lighting system, a locking system, a calibration system, and a ranging system. In some embodiments, the embedded computer or PLC controls 1, 2, 3, 4, 5, 6, 7, 8, 9, 10, 11, 12, or more systems.

In some embodiments, the apparatus comprises components for implementing a disinfection cycle that can be controlled electronically using a Human Machine Interface (HMI) display panel or display device (e.g., an LCD panel) on the outer surface of the cabinet. In order to easily locate apparel (e.g., white coats, scrubs, etc.), in some embodiments the cabinet is fitted with a radiofrequency identification (RFID) reader or a barcode reader containing identification information. The identification information is combined with radiofrequency means of acquiring identification information about the apparel (e.g., such as when a coat was put into the apparatus or removed from the apparatus), with means of acquiring information characterizing the disinfection cycle, and with means of combining identification information about each item of apparel in order to generate traceability information about the disinfection status of each item of apparel. The information collected can be stored in a computer or a programmable logic controller (PLC) in the disinfection apparatus or in a networked computer used to gather information and communicated to other computers or individuals. In some embodiments, the apparatus and/or the apparel and accessories are fitted with appropriate devices to send reminders to the users to disinfect the apparel and accessories at regular or predetermined time intervals.

FIGS. 1A-D depict an exemplary disinfection apparatus 100 in which the apparel to be disinfected 118 is stationary within a cabinet 101 and the disinfecting agent comprises UV emitted from a UV lamp 111 that moves around the apparel 118. FIG. 1A illustrates the front view of this apparatus. FIG. 1B illustrates the side view of this apparatus. In this embodiment, the apparatus comprises the following components: Cabinet 101, X-axis guide rod assembly 102, X-axis feed drive assembly 103, Slide Plate 104, stainless steel (SS) reflector sheets 105, Y-axis guide rod assembly 106, Y-axis feed drive assembly 119, Intermediate panel 107, Top panel 108 Electrical cabinet 109, Hanger mounting assembly 110, UV lamps 111, Hangers 112, Wheels 113, Y-axis stepper motor 114, and X-axis stepper motor 115. These components are described in further detail below. FIG. 1C illustrates the front view of an alternative configuration of the embodiment illustrated in FIGS. 1A and 1B. In this configuration, the cabinet does not include internal panels and slide assemblies, but includes an RFID reader 116 and Human Machine Interface (HMI) 117 on the front face of the cabinet. FIG. 1D illustrates an exemplary carriage 120 comprising the following components: X-axis stepper motor 115, X-axis guide rod assembly 102, and X-axis feed drive assembly 103.

FIGS. 2A-C depict an exemplary disinfection apparatus 200 in which the apparel to be disinfected 218 is mobile while the UV light moves vertically around the apparel. FIG. 2A illustrates the front view of this apparatus. FIG. 2B illustrates the side view of this apparatus. In this embodiment, a loading zone (space to leave apparel to be disinfected) is configured to hold at least one item to be disinfected or sanitized and an unloading zone is configured to hold at least one item that has been disinfected or sanitized. In this embodiment, the apparatus comprises the following components: Cabinet 201, Vertical axis slide assembly 202, UV-lamps 213, Horizontal axis slide assembly 204, Ball lock pins 205, Hanger unload assembly 206, Intermediate panel 207, Motorized actuator 208, Electrical cabinet 209, Hangers 214, X-axis servo motor 211, Y-axis servo motor 212, and horizontal motion assembly 215. These components are described in further detail below. FIG. 2C illustrates the front view of an alternative configuration of the embodiment illustrated in FIGS. 2A and 2B. In this configuration, the cabinet does not include internal panels and slide assemblies, but includes an RFID reader 216 and Human Machine Interface (HMI) 217 on the front face of the cabinet.

In some embodiments, the apparatus of the present invention includes the components described below. These components are described by way of example in conjunction with FIGS. 1A-D and FIGS. 2A-C.

Cabinet

The cabinet (FIG. 1A-101, FIG. 2A-201) serves as the housing for all internal equipment as described herein that is used to perform disinfection and control the systems of the apparatus and for holding one or more items of medical or laboratory apparel and/or accessories. In certain embodiments, the cabinet is a container, wardrobe, cupboard, or other repository for hanging one or more items of medical or laboratory apparel and/or accessories. In some instances, the cabinet comprises one or more shelves for holding one or more items of medical or laboratory apparel and/or accessories. The cabinet comprises one or more doors to access the interior of the cabinet. In some embodiments, the cabinet comprises double doors. In some embodiments, the exterior of the cabinet has a handle with a locking mechanism that is used to open the cabinet doors to access the medical or laboratory apparel (FIG. 1B-118, FIG. 2B-218) and/or accessories inside. In some embodiments, the cabinet is constructed of metal. The cabinet has two or more wheels (FIG. 1B-113) to facilitate transportation of the cabinet in some non-limiting embodiments.

In general, the cabinet when closed is completely sealed (e.g., with proper seals and physical barriers) to prevent any disinfectant (e.g., UV light) from escaping the inside of the cabinet. In some embodiments, the cabinet comprises a locking system. The locking system prevents access to the interior of the cabinet to prevent user exposure to UV illumination or other disinfecting agents. In some embodiments, the locking system functions to keep users secure from the UV or other disinfection agents that are used in the apparatus. As a non-limiting example, the cabinet is equipped with a physical handle with a locking mechanism. The state of the lock is controlled via the embedded computer or PLC. The user gains access to the cabinet by using a radio-frequency identification (RFID) card, passcode, or other access methods. Once access is granted, the lock is released and the user is able to open the cabinet by using the handle located on the cabinet doors. When access is not granted, the cabinet remains locked and access to the cabinet via the handle is not possible. Once an electronic signal is sent for the lock to open, another electronic signal is sent to ensure that the UV light source (FIG. 1B-111, FIG. 2B-213) or other disinfectant source inside the cabinet is turned off. In some embodiments, the locking system further comprises a physical switch mounted on a cabinet door that deactivates when the door of the cabinet is open.

In some embodiments, the cabinet comprises a door that either opens out or slides to access the interior of the cabinet. In some embodiments, the sliding door is made of a material that is substantially impermeable to UV radiation or is coated with a layer of a material that is substantially impermeable to UV radiation. For example, in some embodiments, the sliding door is made of glass, polycarbonate, or acrylic. In some embodiments, the sliding door is a self-closing sliding door. In some embodiments, the sliding door remains in a closed position, e.g., via a locking system, unless a user opens the door using an appropriate access protocol, e.g., as described herein. Sliding door assemblies for cabinets are known in the art. See, e.g., WO 2006/113773, incorporated herein by reference.

Figure 1B:
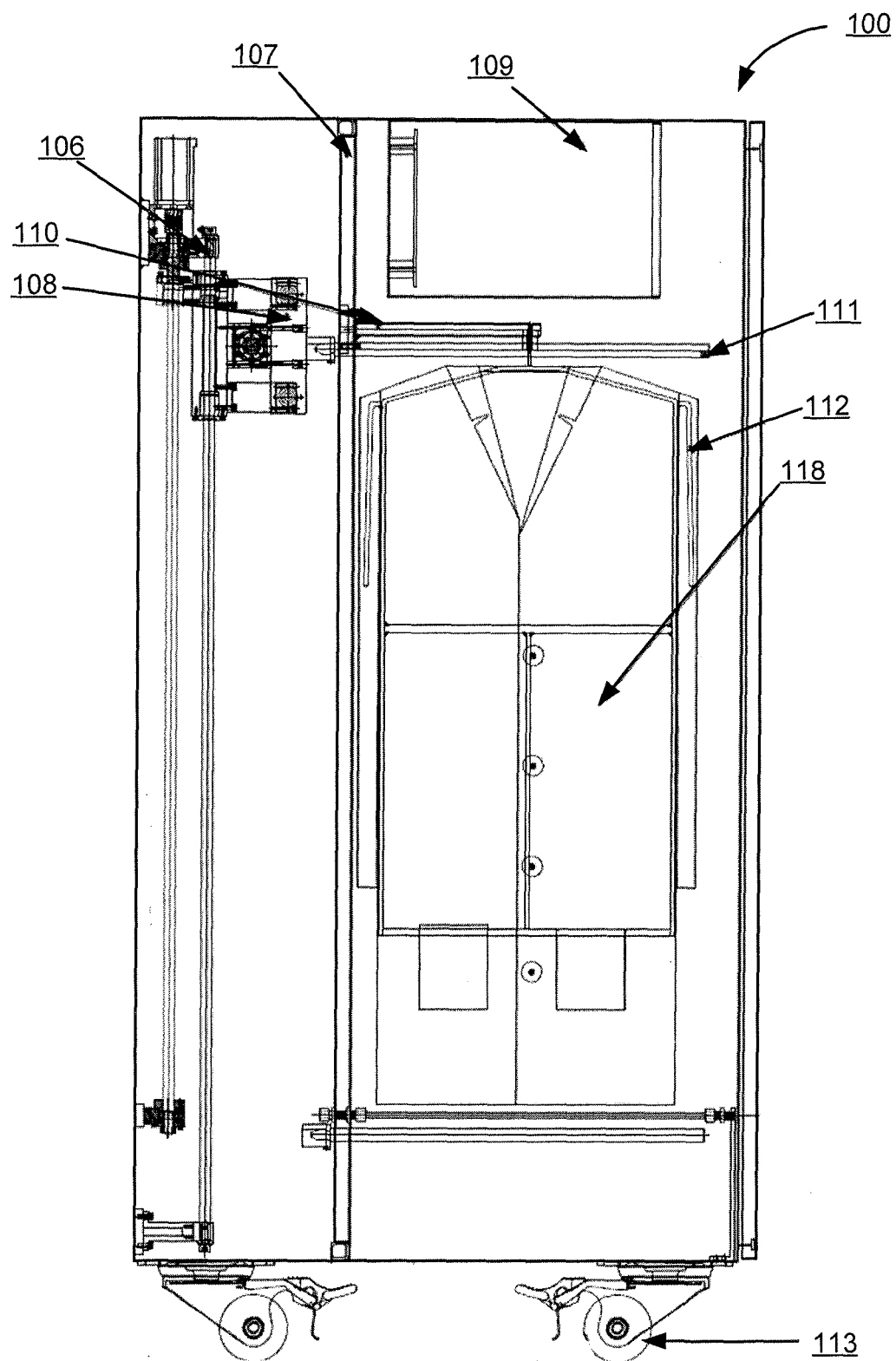
FIG. 1B illustrates the side view of an exemplary disinfection cabinet in accordance with an embodiment of the invention.

In some embodiments, the interior of the cabinet is partitioned into two or more partitions in order to keep multiple items of medical or laboratory apparel and/or accessories separate. In some embodiments, one or more interior surfaces of the cabinet are made of or coated with a reflective material, such as stainless steel (SS) reflective sheets (FIG. 1A-105). In some embodiments, the cabinet further comprises hangers (FIG. 1B-112, FIG. 2B-214) that are especially designed to hold the medical or laboratory apparel in positions that will maximize the exposure of the apparel to the disinfectant. In some embodiments, the hangers are positioned in front of an intermediate panel (FIG. 1B-107; FIG. 2B-207) that partitions the areas of the cabinet in which various motors and rods are housed and areas in which apparel and accessories are housed.

Figure 2A:
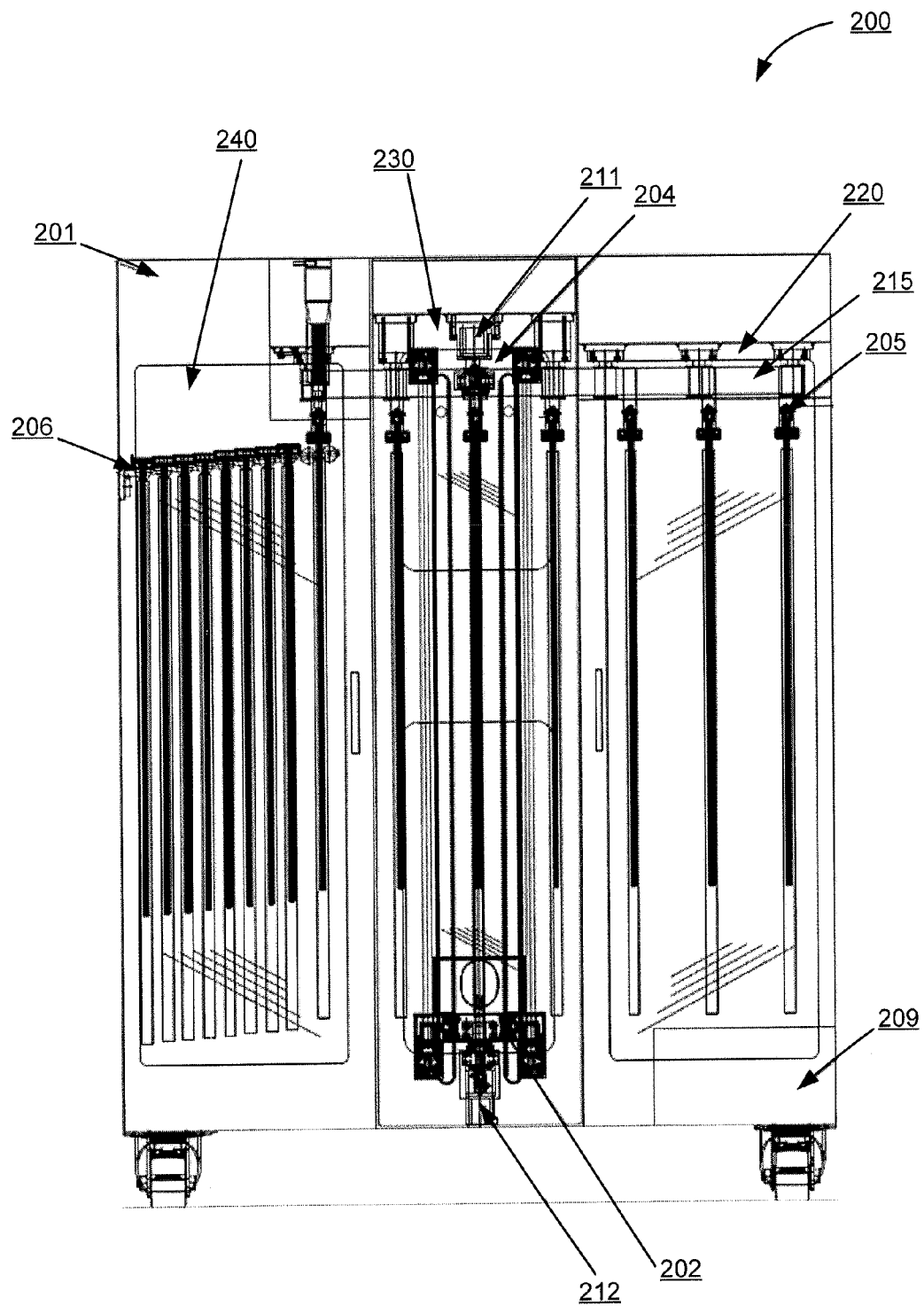
FIG. 2A illustrates the front view of an exemplary disinfection cabinet with a UV scanning device in accordance with an embodiment of the invention.
Figure 2B:
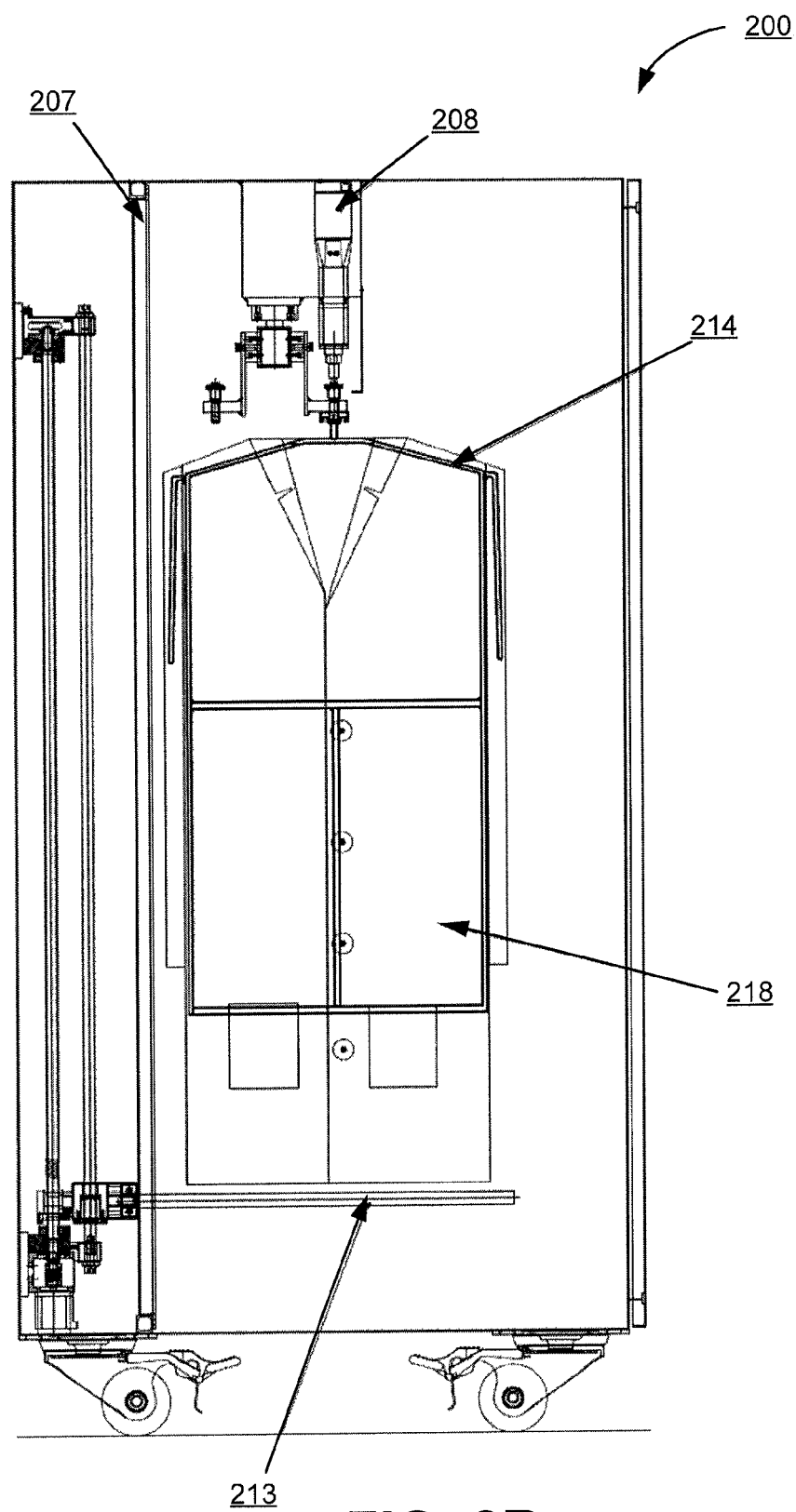
FIG. 2B illustrates the side view of an exemplary disinfection cabinet in accordance with an embodiment of the invention.

FIG. 2A illustrates an exemplary apparatus (FIG. 2A-200) in which the disinfection cabinet comprises three dedicated zones. A first zone (FIG. 2A-220) (i.e., "loading area") is dedicated to receiving apparel and/or accessories for disinfection. A second zone (FIG. 2A-230) (i.e., "scanning area") is dedicated to implementing the disinfection process, through which the apparel and/or accessories to be disinfected pass and are exposed to a disinfecting agent. A third zone (FIG. 2A-240) (i.e., "unloading area") is dedicated to storing the apparel and/or accessories after the disinfection process has been completed. In some embodiments, a set of hangers on which one or more items of apparel and/or accessories are placed is moved from the loading area to the scanning area and then transferred to a hanger unload assembly (FIG. 2A-206) in the unloading area by a motorized drive system. For example, in one embodiment, a hanger (FIG. 2B-214) engages a horizontal axis assembly via ball lock pins (FIG. 2A-205). A motorized actuator (FIG. 2B-208) disengages the hanger from the assembly, allowing it to drop onto the hanger unload assembly (FIG. 2A-206). In other embodiments, a horizontal axis on which the hanger mounting assembly is engaged enables this movement to be performed manually (e.g., by pushing and/or pulling a set of hangers from one zone to the next along a track).

In some embodiments, the interior of the cabinet further comprises a lighting system comprising one or more lighting sources that are distinct from a lighting source used in the disinfecting system. In some embodiments, the lighting source comprises white LEDs positioned within the interior of the cabinet. The purpose of this lighting is to make it easier to see inside the cabinet when depositing or removing an item of medical or laboratory apparel or an accessory. Additionally, it is useful for cases where maintenance needs to be performed on the cabinet.

In some embodiments, the cabinet further comprises a physical power connection and/or an emergency shutoff switch (e.g., on the exterior of the cabinet).

Scanning System

Figure 1C:
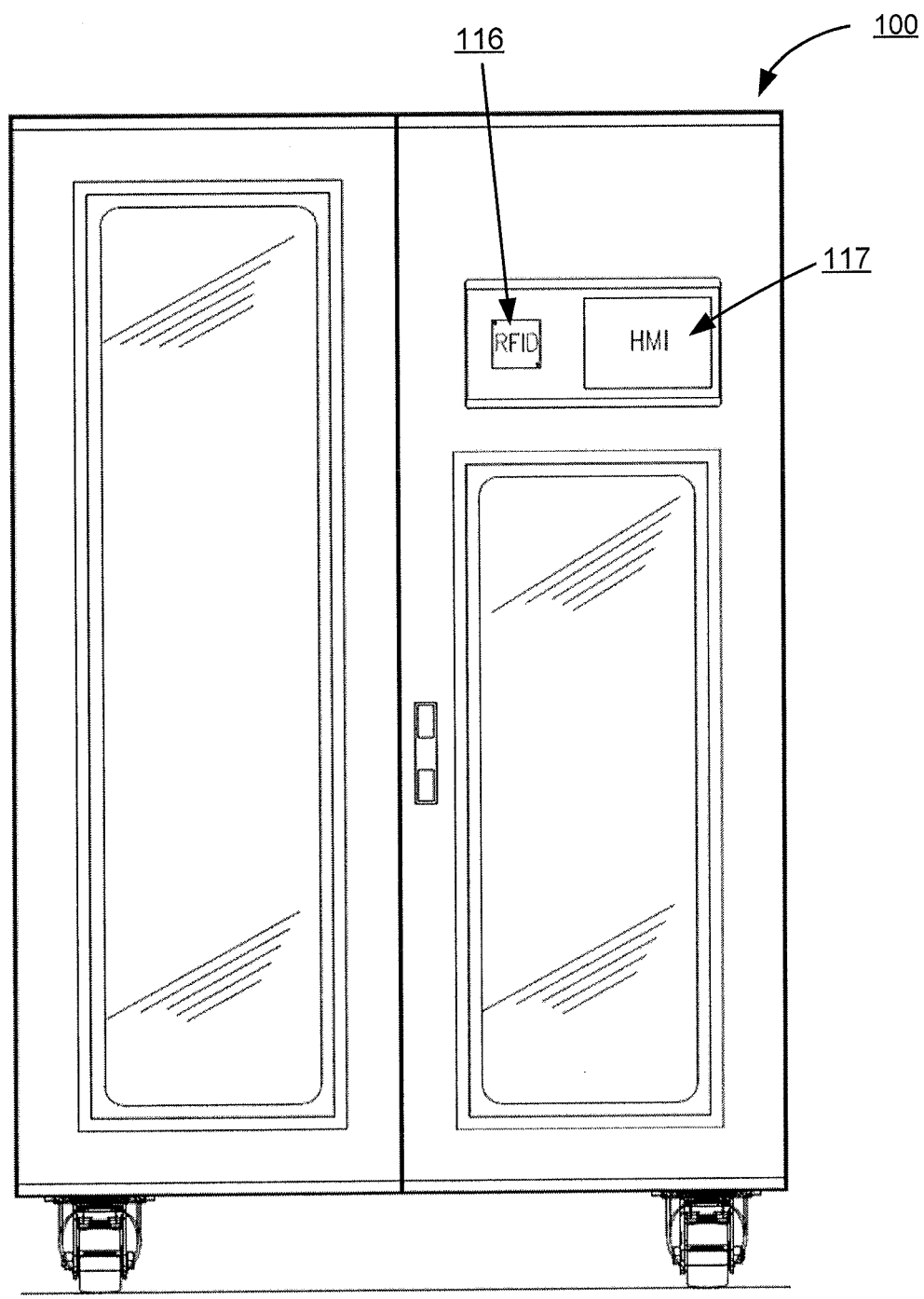
FIG. 1C illustrates the front view of an exemplary disinfection cabinet without internal panels and slide assemblies but with an RFID reader and Human Machine Interface in the front in accordance with an embodiment of the invention.
Figure 1D:
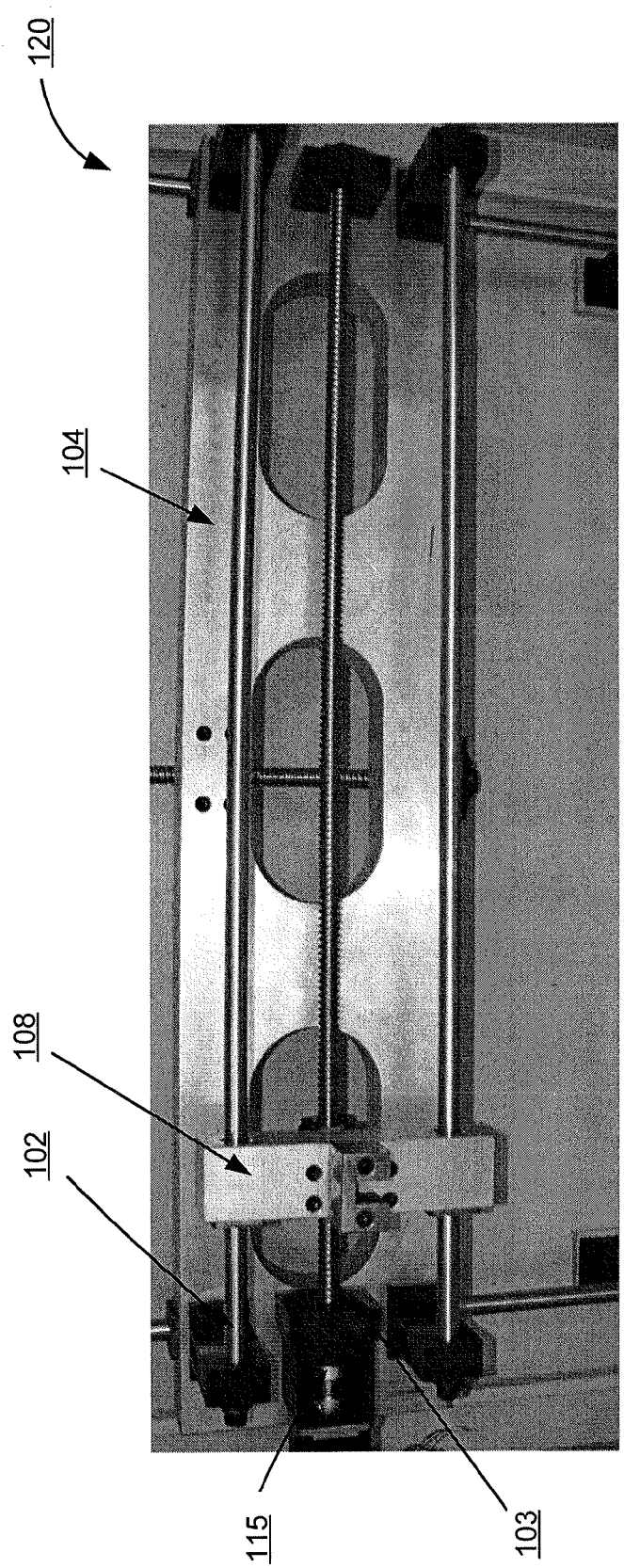
FIG. 1D illustrates an exemplary carriage in accordance with an embodiment of the invention.

In some embodiments, the apparatus comprises a scanning system housed within the cabinet. For example, in the embodiment illustrated in FIG. 1A, the scanning system comprises a support frame, a Y-axis guide rod assembly 106, a Y-axis feed drive assembly 119, a Y-axis stepper motor 114, a slide plate 104, and a carriage mounted on the slide plate. As depicted in FIG. 1D, an exemplary carriage 120 comprises an X-axis guide rod assembly 102, an X-axis feed drive assembly 103, and an X-axis stepper motor 115. In alternative embodiments, the X-axis stepper motor is a servo motor or other mechanical motor. In other embodiments the carriage also comprises SS reflector sheets. In some embodiments, the disinfecting system is mounted on the carriage. The carriage carrying the source of disinfection can move either horizontally, vertically, both horizontally and vertically, or in a circular motion. In mathematical terms, this motion can be defined as movement along the X axis, Y axis, or Z axis. In some embodiments, the carriage moves along an XY axis, a YZ axis, and/or an XZ axis. In some embodiments, the carriage moves along an XYZ axis.

In some embodiments, the scanning system is an XY linear slide that can relocate a carriage mounted on it to any location within the confines of the cabinet. In some embodiments, the XY linear slide is mounted onto one or more walls of the cabinet. In general, the scanning system couples two linear sub-systems—one for horizontal motion and the other for vertical motion. By mounting one sub-system on top of the other (e.g., the horizontal linear sub-system atop the vertical linear sub-system), any coordinate location within the XY plane is reached by systematically controlling each sub-system. In some embodiments, the scanning system is a commercially available system from, for example, PBC Linear® (Roscoe, Ill.), NSK Americas (Ann Arbor, Mich.), and Thomson Industries, Inc. (Wood Dale, Ill.).

Horizontal and Vertical Linear Sub-Systems:

In one embodiment, horizontal linear translation is achieved by using a vertically mounted motor such as a DC or stepper motor (FIG. 1A-114, 115) or servo motor (FIG. 2A-211, 212), or other mechanical power source. Gears may be used to transmit the torque from the rotating motor in order to turn shafts, gears, belts, pulleys, and/or other accessories that cause the system to spin. For example, a linear slide, such as a horizontal axis slide assembly (FIG. 2A-204), driven by the motor is rigidly affixed to a vertical bar or top panel. An exemplary horizontal axis slide assembly is further illustrated in FIG. 1D. In this embodiment, the horizontal axis slide assembly comprises a carriage 120 that further comprises an X-axis guide rod assembly 102, an X-axis feed drive assembly 103, an X-axis stepper motor 115, and a top panel 108 mounted on a slide plate 104. In this example, the motion of the X-axis stepper motor drives the X-axis feed drive assembly, which causes the top panel to move horizontally along the X-axis guide rod assembly. In some embodiments, to reduce the effect of friction, the bar or top panel is mounted on a support frame using wheels or ball bearings. Vertical linear translation is achieved by a similar mechanism as for the horizontal linear sub-system, except that the bar and motor are mounted horizontally. For example, a linear slide, such as a vertical axis slide assembly (FIG. 2-202), driven by a motor is rigidly affixed to a horizontal bar. The motion of the motor causes the horizontal bar to move vertically. In some embodiments, the horizontal and/or vertical sub-system motors interface to an embedded computer or a programmable logic controller (PLC) within the cabinet with a motor controller board.

Carriage:

The scanning system comprises a carriage that is mounted on, and can move along, the slide. In some embodiments, the carriage transports the disinfecting system along the slide (e.g., along an XY axis, a YZ axis, an XZ axis, or an XYZ axis). FIG. 1D illustrates an exemplary carriage 120 comprising an X-axis guide rod assembly 102, an X-axis feed drive assembly 103, an x-axis stepper motor 115 and top panel 108 mounted on a slide plate 104 that engages a Y-axis feed drive assembly 119 and is moveably affixed to a Y-axis guide rod assembly 106. In some embodiments, the disinfecting system is mounted to the top panel of the carriage. Carriages suitable for use in slide systems are known in the art and are readily commercially available from, for example, PBC Linear® (Roscoe, Ill.), NSK Americas (Ann Arbor, Mich.), and Thomson Industries, Inc. (Wood Dale, Ill.).

Disinfecting System

The disinfecting system comprises one or more disinfecting agents that can inactivate, reduce, or eliminate pathogens. In some embodiments, the disinfecting agent is a source of ultraviolet (UV) radiation, a source of infrared light, or a chemical. In some embodiments, the disinfecting system comprises one or more sources of UV radiation. Sources of UV radiation include, but are not limited to, UV lamps (FIG. 1B-111, FIG. 2-213), such as UV mercury vapor lamps, UV light-emitting diodes (LEDs), UV deuterium lamps and UV metal halide lamps containing mercury, gallium iodide, iron iodide or other metal iodides that alter the spectral output of the lamp. In some embodiments, the disinfecting system comprises one or more sources of chemicals that are harmful or toxic to pathogens. For example, in some embodiments the disinfecting system comprises one or more chemical sprays, such as but not limited to hydrogen peroxide. In some embodiments, the disinfecting system comprises one or more sources of infrared light, e.g., an infrared lamp, to disinfect and/or dry. In some embodiments, the disinfecting system comprises at least one source of UV radiation and at least one chemical spray. In some embodiments, the disinfecting system comprises at least one source of UV radiation, at least one chemical spray, and at least one source of infrared light.

In some embodiments, the disinfecting system is mounted in a stationary position within the cabinet. In some embodiments, the disinfecting system is mounted on a carriage that can move along a slide, e.g., horizontally, vertically, and/or circularly in a predetermined path. By being mounted on the carriage, the disinfecting system (e.g., UV light source and/or chemical spray) is able to move horizontally and vertically in the cabinet, in order to maximize the exposure of the disinfectant to the medical or laboratory apparel or accessories in the cabinet, which in turn will increase or improve the anti-pathogenic effect. One of skill in the art will recognize that parameters such as light intensity, distance from disinfectant source (e.g., light source) to items to be disinfected, and rate of travel of the disinfecting system on the carriage can be optimized. In some embodiments, the other forms of disinfectants described herein can also be optimized. In some embodiments, the apparatus comprises both a disinfecting system that is mounted on a carriage that moves along a slide and one or more disinfecting systems that are mounted in a stationary position within the cabinet. In embodiments wherein the apparatus comprises two or more disinfecting systems (stationary and/or mounted on a carriage that moves along a slide), the two or more disinfecting systems can comprise the same type of disinfecting agents (e.g., a UV light source) or different types of disinfecting agents (e.g., a UV light source and a chemical spray).

In embodiments where the disinfecting system is a UV light source (e.g., mercury vapor lamps or a LED), the apparatus will further comprise certain electrical connectors and support equipment that regulate the lamp and/or LEDs, provide the right amount of current, and determine whether the light sources have successfully turned on or remained off when switched on. This support equipment enables troubleshooting and provides warnings regarding required maintenance, e.g., when a lamp burns out and needs to be changed. Where the disinfecting system is a chemical spray system, nozzles are mounted on the carriage and tubing is attached in a protected conduit to carry the disinfecting chemicals. Additionally, the apparatus can further comprise electrical connections to regulate the spraying of chemicals.

In some embodiments, the disinfecting system comprises a chemical disinfectant sub-system. In some embodiments, the chemical disinfectant sub-system comprises: a tank with a pump, a level indicator, a pressure indicator, hosing, and one or more sprayers.

Garment Identification/Tracking System

In some embodiments, the apparatus comprises a garment identification system. This system is used to determine the identity of the apparel (e.g., the coats, scrubs, uniforms, aprons, or shoes) and/or accessories being disinfected or sterilized. In some embodiments, the identity of the apparel or accessories is determined using a radio-frequency identification (RFID) reader mounted on the carriage. In some embodiments, an RFID reader is located internally and/or externally on the cabinet. As the carriage moves horizontally or vertically, the reader polls for identification tags (e.g., RFID tags) in its vicinity. When such a tag is detected, the identity of the sensor is read and transmitted to the central computer or PLC, which may be located in the electrical cabinet (FIG. 1A-109, FIG. 2A-209), along with the location of the carriage where the sensor was read. Thus, in some embodiments, the garment identification system comprises one or more identification tags or indicators (e.g., RFID tags), wherein each identification tag is associated with a garment, and a tag or code reader (e.g., an RFID reader), wherein the tag or code reader is mounted on the carriage. In some embodiments, the identification tag(s) or indicator(s) are attached to or associated with hangers onto which garments can be hung. In some embodiments, the identification tag(s) or indicator(s) are attached to an item of apparel. In some embodiments, the garment identification or tracking system comprises a barcode reader mounted on the carriage or at a suitable location in or on the cabinet and a barcode tag for each of the one or more items of medical or laboratory apparel and/or accessories.

In some embodiments, the embedded computer or PLC receives data from the garment identification or tracking system and has the ability to send electronic messages to users based on this data. For example, the embedded computer analyzes data received from the tracking system and sends reminders to users to disinfect their apparel at regular or pre-determined intervals, or upon the occurrence of certain events. In one embodiment, the embedded computer or PLC sends a reminder to the mobile phones of healthcare staff to disinfect their lab coats at regular intervals. For example, a reminder is sent at the end of every 8 hour workday, or more frequently if there is a known bacterial, viral or other pathogen outbreak. In some embodiments, the embedded computer or PLC sends reminders to users to wash their apparel and/or accessories at pre-determined time intervals. In a particular embodiment, the embedded computer or PLC sends reminders at pre-determined time intervals in addition to reminders to regularly disinfect apparel and/or accessories. In some embodiments, the embedded computer or PLC determines that a user's apparel has not been disinfected within a previously set amount of time and transmits a reminder to the user's cell phone and e-mail address at regular intervals until the apparel is disinfected. In particular embodiments, the embedded computer or PLC captures disinfection status information on each item of medical or laboratory apparel and/or accessory and processes the data for usage analysis or for providing status updates to users.

Hanging System

In some embodiments, the apparatus comprises a system for hanging garments. In some embodiments, the hanging system comprises a hanger mounting assembly (FIG. 1B-110), one or more rails or rods and one or more hangers (FIG. 1B-112, FIG. 2B-214). Hangers can be configured in either fixed positions or dynamic positions. The fixed hanger position system has a set number of positions within the cabinet in which the items of apparel can be hung. These positions restrict where the hangers sit within the cabinet. In some embodiments, the hanger positions are evenly spaced to ensure that enough space exists between apparel so that they can be scanned while hanging in the cabinet. The dynamic hanger system allows for more apparel to be hung within a single cabinet system by allowing the hangers to be repositioned within the cabinet. In cases where a garment needs to be either scanned or removed, hangers on either side of the hanger of interest can be moved to create additional space between the hanger of interest and neighboring hangers. This arrangement provides plenty of spacing on both sides of the garment to allow for the scanning subsystem to position the disinfection subsystem in the correct positions for disinfection. The dynamic hangers slide on a rail.

In some embodiments, the hanging system comprises a horizontal motion assembly (FIG. 2A-215) onto which hangers are removably attached via ball lock pins (FIG. 2A-205). In some embodiments, the horizontal motion assembly is driven by a conveyor belt drive system. In some embodiments, the hangers are moved horizontally along the horizontal axis by a conveyor belt drive system and disengaged from the assembly by a motorized actuator (FIG. 2B-208) that transfers the hangers to an unload assembly (FIG. 2A-206). For example, a hanger attached to the horizontal motion assembly via a set of ball lock pins is driven from a loading area of the cabinet along the horizontal axis to a disinfection area of the cabinet by a conveyor belt where any items on the hanger are sanitized. When disinfection has been completed, the conveyor moves the hanger along the horizontal axis to a post-disinfection area of the cabinet and the motorized actuator engages the set of ball lock pins to release the hanger from the horizontal motion assembly, allowing it to drop onto the unload assembly.

Hanger State Measurement System

In some embodiments, the apparatus comprises a hanger state measurement system. Each hanger in the cabinet exists in one of two states—either loaded with apparel (e.g., holding a coat) or without (e.g., not holding a coat). In order to measure the presence or absence of apparel on a hanger, a pressure or weight sensor is mounted on a surface on which a portion of the hanger rests. Each pressure or weight sensor is connected to the embedded computer or PLC either directly or indirectly via intermediate processing units such as microcontrollers and control boards connected to the embedded computer or PLC. The embedded computer or PLC receives and compares a load value associated with the weight or pressure measured by the sensor to a threshold value or values in a pre-calibrated range. Based on this comparison, the hanger state is set accordingly. For example, the PLC compares a load value of 425 grams received from a weight sensor to a threshold value of 415 grams and sets the hanger state to loaded. In some embodiments, the status of a hanger is determined by the state of a button or switch that is pressed or toggled when a hanger is loaded with an item of apparel or accessory and not pressed or not toggled when the hanger is not loaded with an item of apparel or accessory.

Hanger Indicators

In some embodiments, the apparatus comprises an indicator associated with each hanger (e.g., above each hanger or on each hanger) to allow a healthcare worker, laboratory worker, or other user of the apparatus to identify his/her garment or garments in the cabinet as it is being accessed. The status of each indicator is controlled by the embedded computer or PLC. The apparatus keeps track of and records the location of each garment as it is loaded onto and removed from a hanger. When a garment is loaded onto a hanger, the hanger indicator turns on. This is accomplished by the toggling of a physical switch or pressing of a button on each hanger or reading of position identifiers as a garment is scanned. Once the garment is removed from the hanger, the hanger indicator turns off. For example, the hanger indicator on a hanger illuminates when a physical switch is toggled by the positioning of a lab coat on the hanger. In some embodiments, the hanger indicator can also be used to instruct the health care worker, laboratory worker, or other use where to hang apparel. In some embodiments, the hanger indicator is a light source, such as an LED.

Locking System

In some embodiments, the apparatus comprises a locking system to prevent unauthorized access to the interior of the cabinet or to prevent user exposure to UV illumination or other disinfecting agents in use in the apparatus. For example, the cabinet is equipped with a physical handle with a locking mechanism, such as a pin tumbler handle lock or mechanical key pin code lock. In some embodiments, the state of the lock is controlled via the embedded computer or PLC. In a particular embodiment, a user gains access to the cabinet by using a radio-frequency identification (RFID) card. In other embodiments, a user gains access to the cabinet by using a pre-assigned passcode or by any other suitable method for providing access credentials to the apparatus. Once access is granted, the lock is released and the user is able to open the cabinet by using a handle located on the cabinet doors. If access is not granted, the cabinet remains locked and access to the cabinet via the handle is not possible. In embodiments where the state of the lock is controlled by the embedded computer or PLC, the embedded computer or PLC transmits an electronic signal to the lock for the lock to open and another electronic signal is sent to ensure that the UV light source or other disinfectant source inside the cabinet is turned off. In some embodiments, the locking system further comprises a physical switch mounted on a cabinet door that deactivates the disinfectant source when the door of the cabinet is open.

Figure 2C:
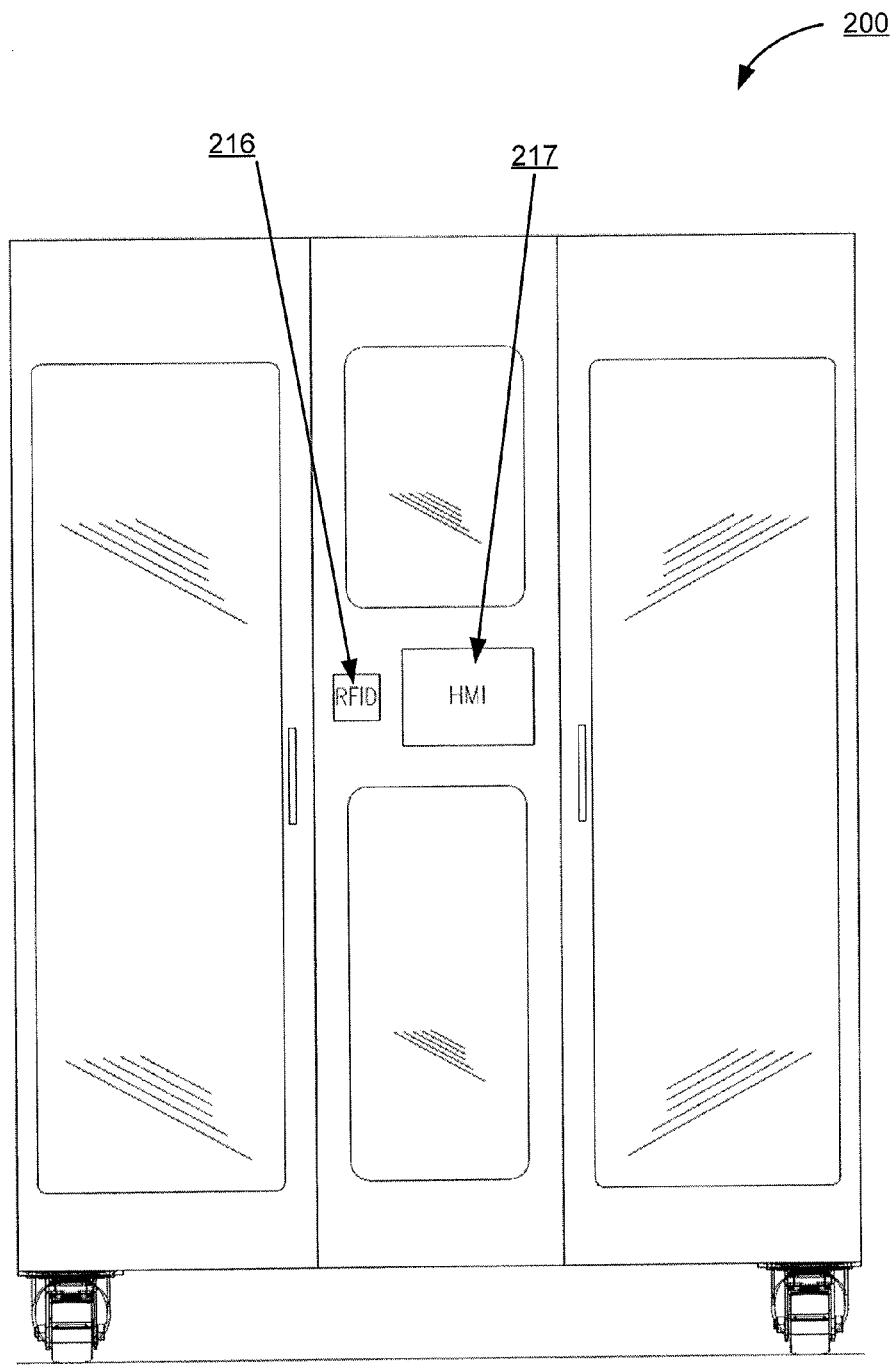
FIG. 2C illustrates the front view of an exemplary disinfection cabinet without the internal panel, but with an RFID reader and Human Machine Interface in the front in accordance with an embodiment of the invention.

In some embodiments, the apparatus comprises devices to enable authorized access to the inside of the cabinet. For example, an RFID reader (FIG. 1C-116, FIG. 2C-216) is mounted on the outside of the cabinet as illustrated in FIG. 1C and FIG. 2C. The RFID reader allows the apparatus to identify a user via an assigned identification card. If the identification presented is authorized, the cabinet is unlocked so that the user can open it. As another non-limiting example, entry to the unit is enabled using an assigned passcode. This is done either on a physical keypad or on a digital keypad displayed on a touch screen. Entry to the unit is only allowed when the proper passcode is entered. In some embodiments, the apparatus comprises both an RFID and a passcode option for entry.

Human Machine Interface

In some embodiments, the apparatus comprises a Human Machine Interface (HMI) (FIG. 1C-117, FIG. 2C-217) comprising a display mounted to the outside of the cabinet that is visible to users. A screen (e.g., a touchscreen) on the display serves as the interface point for users interacting with the cabinet. For embodiments wherein access to the cabinet is granted via entering a passcode, the touchscreen displays a keypad on the screen. For embodiments wherein an RFID reader is used or after access has been granted via the touchscreen keypad, the touchscreen displays relevant information to the user. For example, once a user is properly identified, the screen displays relevant information such as the status of the apparatus and/or the items inside. Possible display information includes, but is not limited to: disinfection status of an item of medical or laboratory apparel within the cabinet; location of the item within the cabinet; statistics of cabinet usage; location of items of medical or laboratory apparel throughout all cabinets in the system; disinfection options; control parameters including disinfection time; and an interface for maintenance or assistance. In some embodiments, the touchscreen is driven by the embedded computer or PLC held within the cabinet enclosure.

Calibration System

In some embodiments, the apparatus comprises a calibration system. The primary purpose of the calibration system is to determine the true location of the carriage when it comes in contact with the support frame of the scanning system. As a non-limiting example, this can be achieved via limit switches that get pushed when the carriage touches any part of the frame (both horizontal and vertical directions). Another non-limiting example uses precise rotation encoders for the motors and performs a calibration procedure in order to determine the motion constraints along the horizontal and vertical directions.

Ranging System

In some embodiments, the apparatus comprises a ranging system. The ranging system is mounted on the carriage of the scanning system in order to measure the distance between the carriage and the nearest object inside the cabinet. A ranging system can be constructed, for example, using ultrasound distance measuring devices.

Internal Storage Box

In some embodiments, the apparatus comprises an internal storage box. This box can be used to store spare components for the apparatus (e.g., spare light bulbs) or to store components, such as bulbs, that need to be disposed.

Embedded Computer/Programmable Logic Controller

An embedded computer or a programmable logic controller (PLC) in the cabinet controls one or more of the systems of the apparatus, either through direct connection or indirectly via dedicated micro-controllers that in turn interface with the various systems. In some embodiments, the embedded computer or PLC is a microcontroller. In other embodiments, other computing devices like a personal computer can be used instead of a PLC. In some embodiments, the embedded computer or PLC is housed in the interior of the cabinet, such as in the electrical cabinet (FIG. 1B-109, FIG. 2A-209). The embedded computer or PLC contains the software protocols that ensure the proper functionality of the apparatus. In some embodiments, the embedded computer or PLC connects to the Internet via Ethernet or WiFi and transmits information to central servers in the network, additional computers in the network and/or users of the apparatus. In a particular embodiment, the embedded computer or PLC transmits data to a computer connected to the apparatus via a network. The computer comprises software that, when executed, communicates information associated with the data to one or more individuals or additional computers. In some embodiments, the embedded computer or PLC has the ability to send electronic messages to users. For example, the embedded computer or PLC sends electronic messages to users via text messaging, SMS messaging, e-mail messaging, instant messaging, voice messaging, or any other electronic transmission suitable for communicating messages to users of the apparatus. This will be used to send reminders to users to disinfect their apparel and/or accessories at regular and/or pre-determined intervals. For example, the PLC in one embodiment sends a reminder to healthcare staff to disinfect their lab coats at regular intervals, such as at the end of every 8 hour workday or more frequently if there is a known outbreak of a certain bacterial, viral or other pathogen outbreak or for other administrative reasons.

The computer may be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, may be included. Where the computer is attached to a network, the connections may be provided via any suitable transport media (e.g., wired, optical, and/or wireless media) and any suitable communication protocol (e.g., TCP/IP); the host computer may include suitable networking hardware (e.g., modem, Ethernet card, WiFi card). The computer may implement any of a variety of operating systems, including UNIX, Linux, Microsoft Windows, MacOS, or any other operating system.

Computer code for implementing aspects of the present invention may be written in a variety of languages, including BASIC, PERL, C, C++, Java, JavaScript, VBScript, AWK, Python, Ladder logic, Stage logic, function block diagram, Stage transition diagrams, instruction list (IL), sequential functional chart, or any other scripting or programming language that can be executed on the embedded computer or PLC, or that can be compiled to execute on the embedded computer or PLC. Code may also be written or distributed in low-level languages such as assembler languages or machine languages.

In some embodiments, the apparatus comprises at least 1, 2, 3, 4, 5, 6, 7, 8, 9, 10, 11, 12, 13, 14, 15, 16, 17, 18, 19, 20, 21, 22, or all of the following components: Embedded/small form factor computer or programmable logic controller (PLC); Digital I/O; Motor controllers; Power relays; Light sensors; Hanger switches; Limit switches; Mechanical assembly; Facility to hold apparel and/or accessories; Storage unit for extra bulbs; Locking mechanism; Carriage; RFID reader on carriage; Bulb Ballast; Multiple bulbs; Routing for cabling; UV light source for disinfecting; Display for accessing the cabinet; Hanger(s); Emergency power shut-off; Wired/wireless adapter; Apparel and/or accessory identification system such as RFID or barcode tags and RFID or barcode readers; and/or RFID reader on external cabinet.

III. Processes for Disinfecting and/or Sterilizing Medical or Laboratory Apparel and Accessories One function of the apparatus of the present invention is to disinfect items of apparel, garments and accessories of health care providers and laboratory workers. In order to achieve the task of disinfecting such items, the components of the apparatus must interact with each other and with the individual users of the apparatus via certain processes, which may include 1, 2, 3, 4, 5, or all of the following processes. An embedded computer or a programmable logic controller (PLC) in the cabinet controls all of these processes, either through direct connection with the various systems that carry out each of the processes or indirectly via dedicated micro-controllers that in turn interface with these various systems.

Labeling Process:

Because the cabinet is designed to accommodate multiple items of laboratory or medical apparel and accessories, hanger locations can be monitored to identify the number and location of the items in the cabinet. This information is useful for determining at which hanger locations within the cabinet scan cycles are necessary for the disinfection process. It is also useful for determining which items have already been disinfected so that they are not processed (i.e., put through a disinfection cycle) again. In order to determine this information, the labeling process maintains two lists: a "pre-scan list" and a "post-scan list". The pre-scan list is a list of hanger locations that have not yet been "scanned" (i.e., not yet disinfected). The post-scan list is a list of hanger locations for which a scan cycle has been completed (i.e., a disinfection cycle has been completed).

At any given instance of time when the cabinet door is opened, accessed, and closed, one of four possibilities exist: (a) One or more items of apparel and/or accessories have been added to and removed from the cabinet, (b) One or more items of apparel and/or accessories are only added to the cabinet, (c) One or more items of apparel and/or accessories are only removed from the cabinet, and (d) No items of apparel and/or accessories are added or removed from the cabinet. In some instances where one or more items of apparel and/or accessories are removed from the cabinet and one or more items of apparel and/or accessories are placed in the cabinet for disinfection, sensors (e.g., RFID or other forms) on the apparel and/or accessories communicate information to the embedded computer or PLC to allow the apparatus to differentiate the disinfected apparel from the non-disinfected apparel to avoid repetitious disinfection of the apparel and/or accessories.

In one embodiment, once the door of the cabinet is closed, the states of the hangers are polled via the hanger state measurement system in order to determine which hangers have items of apparel on them and which ones do not. If a hanger is activated (e.g., as determined from information received from a weight sensor or hanger switch), its location is compared to the location of other hangers in the pre-scan list. If the hanger is not included in the pre-scan list, it is added to the pre-scan list. After completion of a disinfection cycle, the hanger is added to the post-scan list. If a hanger is inactivated, its location is compared to the locations of hangers identified in the pre-scan and post-scan lists and removed from each list in which the location is identified. This hanger polling can either be achieved directly by the embedded computer or the programmable logic controller (PLC), or indirectly via a microcontroller that accesses the states of the hanger system. The pre-scan list can either be sorted sequentially by placing the location of the hanger closest to the scanner's default position at the top of the list and the furthest hanger at the bottom of the list, or any other priority based sorting protocol can be used.

Calibration Process:

The scanning system is composed of motors and gears, which may slip during operation, thereby leading to imprecise position estimates. If these imprecisions are not corrected, then they can accumulate over time and cause the system to break down. Thus, in some embodiments it is desirable to recalibrate the scanning system at the end or beginning of every disinfection process. This recalibration is achieved using the calibration system. The calibration system contains sensors that activate when the carriage of the scanner has touched or is about to touch the frame of the scanning system in both horizontal and vertical directions. The calibration process aids in moving the carriage to a predetermined default position. The default position may be located at the bottom right or bottom left corner or at top or bottom positions of the frame of the scanning system. When the calibration process is initiated, the vertical motor is rotated one step at a time until the calibration system senses that the vertical frame of the scanning system has reached a predetermined end point. Subsequently, a similar procedure is adopted by the horizontal motor, which steps downward one step at a time until the calibration system senses that the horizontal frame of the scanning system has reached a predetermined end point. This location is the default start or end position for the scanning process. The calibration function can be performed by the embedded computer or PLC, which can be operated by the HMI.

Disinfection Process:

The disinfection process utilizes the mechanical scanning system, disinfecting system, ranging system, and the garment identification system. These systems are used in unison to disinfect all of the items of apparel and/or accessories that are in the cabinet. When the cabinet door is opened and closed, a single or multiple items of apparel and/or accessories can either be introduced into the cabinet and/or removed from the cabinet. A labeling and calibration process is initiated when the cabinet door is closed. The calibration process determines that the scanning system is correctly positioned to begin scanning. The labeling process determines which hangers have items of apparel on them that need to be disinfected, and which hangers have items of apparel on them that have already been disinfected. The disinfection process is initiated after the labeling process determines the locations of hangers loaded with apparel requiring disinfection. The disinfection process comprises the following protocols:

Scanning Protocol:

The scanning protocol consists of one or more scan cycles for each hanger in the cabinet on which an item of apparel is currently placed. The locations of one or more hangers loaded with an item of apparel to be disinfected are determined by the labeling process and ordered in a pre-scan list. The scanning system relocates the carriage to a fixed start position at a set distance away from the position of the first hanger in the pre-scan list. The scan cycle is initiated by activating the disinfecting system. When activated, the scanner performs an upward sweep followed by a downward sweep of the carriage to expose any apparel on the hanger to the disinfecting agent and returns to the fixed start position for that hanger using any motion protocol. In some embodiments, the scanner performs a downward sweep followed by an upward sweep. Once this vertical sweep is complete, the scanner then translates the carriage to a fixed end position associated with the hanger and another upward-downward sweep commences. Once this latter sweep is completed, the scan cycle for that hanger is complete and the disinfecting system is deactivated if no other apparel and/or accessories are present in the cabinet. The location of the hanger is removed from the pre-scan list and added to the post-scan list. If other apparel and/or accessories are present in the cabinet, the carriage is relocated to a fixed start position at a set distance away from the position of the next hanger on the pre-scan list and the next scan cycle commences as it did for the first hanger on the pre-scan list. After all the hanger locations in the pre-scan list are disinfected, the calibration process is initiated and the carriage returns to its default position.

In one embodiment, a scan cycle comprises moving apparel to be disinfected from a loading zone within the cabinet to a disinfection zone within the cabinet. In this embodiment, the scanner sweeps vertically from top to bottom and vice versa to expose apparel hanging on a hanger in the disinfection zone to the disinfecting agent. The disinfected apparel is then moved to a holding zone within the cabinet where it may be retrieved from a user of the apparatus. The movement of apparel from one zone to another may be performed manually (e.g., pushing or pulling a set of hangers from one zone to the next along a horizontally mounted track on which the hangers are affixed). Alternatively, the movement of apparel from one zone to another may be automated (e.g., driven by a motor that moves a set of hangers along a horizontally mounted track on which the hangers are affixed).

Garment Identification Indicator:

To enable a user of the apparatus to locate an item of apparel or accessory in the cabinet, each item of apparel and/or accessory in the cabinet is associated with a unique identifier that is mapped to the health care professional, laboratory worker, or other user to which it belongs. In some embodiments, a garment identification tag or indicator (e.g., RFID tag) associated with a particular user is activated when the user accesses the cabinet to identify the user's apparel. The garment identification protocol is also useful for monitoring the frequency by which particular items of apparel and/or accessories are disinfected. In one embodiment, the garment identification protocol is initiated when the garment or accessory has been placed in the cabinet. When a scan cycle commences, the garment identification system detects (e.g., via an RFID reader) a unique identifier associated with the item of apparel or accessory that is hung on the hanger at that scan cycle's position. This unique identifier is linked to the associated hanger's position and appended to the hanger's position in the post-scan list at the end of the scan cycle. In a non-limiting embodiment, the apparel and/or accessories can be disinfected without a garment identification protocol.

Motion Protocol:

The scanning system exhibits either a smooth motion protocol at a single rate or at multiple predetermined rates, or a piecewise continuous motion protocol while stopping at fixed intervals for a predetermined duration of time. If there is no ranging system, the scanning system will move upward and downward at the same horizontal location using one of the aforementioned protocols. If a ranging system is used, then the system will determine the closest distance to the item of apparel being scanned and provide a small deviation to the carriage's position in order to avoid colliding with the item of apparel. Likewise, if the carriage is too far away from the item of apparel, the ranging system will provide small deviations to bring the carriage closer to the item of apparel to ensure effective exposure of the disinfecting agent to the apparel.

Interruption Protocol:

If a system is interrupted in the middle of a scan cycle (for example, by a health care worker retrieving a coat), the interruption protocol commences. When a scan cycle is interrupted, the embedded computer or PLC executes software that deactivates the disinfecting system. The carriage of the scanner is translated downward until it touches the bottom of the frame of the scanning system. This movement is guided by feedback received from sensors in the calibration system. The physical lock on the cabinet door remains locked until the disinfecting system is deactivated and the movement of the carriage is complete. Once these steps are completed, the cabinet door unlocks. If the cabinet door is opened and closed, the calibration process commences and the carriage returns to its default state.

User Interface Process:

In some embodiments, the cabinet is equipped with components such as a touch screen, door handles, LEDs, and hanger indicators for simplifying the user's interactions with the apparatus and its systems. These components interact with each other and individual users via certain user interface (UI) protocols, which are listed and described below:

Access Protocol:

The access protocol provides the human machine interface (HMI) and software pipeline for a user to access the cabinet. An access device mounted on the outer surface of the cabinet enables a user to identify himself/herself to the apparatus. If the user is identified, the post-scan list is accessed to determine whether an identifier associated with the user matches an identifier associated with an item for which disinfection has been completed. If a match is found, any active disinfection process is interrupted and the physical lock of the cabinet is deactivated to permit the user to open the cabinet door to retrieve the item. If, however, the item has not yet been disinfected and is in the pre-scan list, then a warning is presented on a screen with a prompt that enables the user to either open the cabinet or continue the disinfection process. If the user follows the prompt to open the cabinet, the disinfection process is interrupted and the physical lock of the cabinet is deactivated. Once the door is opened, a light inside the cabinet turns on and the hanger indicator associated with the relevant hanger (e.g., as determined by the garment ID system) is activated to help the user find his/her item.

Garment Status Protocol:

A HMI mounted on the outside surface of the cabinet enables a user to retrieve and display the status of an item of apparel or accessory in the cabinet. For example, the apparatus receives a pass code via a touchscreen that is associated with a particular item or user, and accesses the pre-scan and post-scan lists to identify an item associated with an identifier that matches the pass code. If the item is included in the post-scan list, the GUI displays a message indicating that disinfection of the item is complete. If the item is not included in the post-scan list but is included in the pre-scan list, the GUI displays an estimate of when disinfection of the item will be complete. This estimate may be based on the product of an average scan cycle time and number of items above the item in the list. In embodiments where multiple cabinets are interconnected (e.g., via a central server), the GUI on any cabinet may be used to determine the physical location of the cabinet that contains a particular item of apparel and/or accessory and corresponding status.

Quickscan Protocol:

A quickscan protocol enables a user to place an item of apparel and/or accessory in the cabinet for immediate or expedited disinfection. Initiation of this protocol places the item in a top position in the pre-scan list for priority disinfection. At the end of the first scan cycle that includes the item, the protocol interrupts any further disinfection process and unlocks the cabinet door to enable the user to retrieve the item before disinfection of additional items continues.

IV. Methods for Disinfecting and/or Sterilizing Medical or Laboratory Apparel

In another aspect, the present invention provides methods for disinfecting or sterilizing one or more items of medical or laboratory apparel. In some embodiments, the method comprises:

(a) placing the one or more items of medical or laboratory apparel and/or accessories in an apparatus comprising (i) a cabinet; (ii) a disinfecting system housed within the cabinet, wherein the disinfecting system comprises at least one disinfecting agent; and (iii) an embedded computer or a programmable logic controller (PLC) housed within the cabinet; and (b) exposing the one or more items of medical or laboratory apparel and/or accessories to the at least one disinfecting agent under conditions suitable for inactivating or killing pathogens; thereby disinfecting or sterilizing the one or more items of medical or laboratory apparel and/or accessories.

In some embodiments, the apparatus further comprises a scanning system housed within the cabinet, the scanning system comprising a slide and a carriage mounted on the slide, wherein the carriage carries the disinfecting system. In some embodiments, the scanning system comprises a slide for horizontal movement, vertical movement, horizontal and vertical movement, or circular movement. In particular embodiments, the apparatus further comprises an identification or tracking system capable of capturing disinfection status information on each item of medical or laboratory apparel and/or accessory and processing the information for usage analysis or for providing one or more status updates to one or more users.

In some embodiments, the embedded computer or PLC controls the disinfecting system. In some embodiments, the embedded computer or PLC controls one or more (e.g., all) systems of the apparatus. In some embodiments, the embedded computer or PLC controls one or more (e.g., all) of the following systems: a disinfecting system, a scanning system, a horizontal linear sub-system, a vertical linear sub-system, a garment identification system, a hanging system, a hanger state measurement system, a human machine interface, a lighting system, a locking system, a calibration system, and a ranging system. In some embodiments, the embedded computer or PLC controls 1, 2, 3, 4, 5, 6, 7, 8, 9, 10, 11, 12, or more systems.

In some embodiments, the method comprises exposing one or more items of medical or laboratory apparel and/or accessories to one or more disinfection cycles (also interchangeably referred to herein as "scan cycles"). In some embodiments, a disinfection cycle consists of a "vertical sweep" in which the disinfecting system mounted on the carriage moves vertically up and down the height or length of the item or the height of the cabinet partition housing the item and a "horizontal sweep" in which the disinfecting system mounted on the carriage moves horizontally from end to end of the width of the item or the width of the cabinet partition housing the item. In some embodiments, the method comprises exposing the one or more items of medical or laboratory apparel and/or accessories to at least between 2 to 3, 4, 5, 6, 7, 8, 9, or 10 disinfection cycles. In some embodiments, wherein multiple items of apparel and/or accessories are housed in the apparatus at the same time, the method comprises sequentially exposing the items to one disinfection cycle before a further disinfection cycle is initiated for any of the items. In some embodiments, wherein multiple items of apparel and/or accessories are housed in the apparatus at the same time, the method comprises exposing one item to multiple disinfection cycles before initiating a disinfection cycle for another item.

In some embodiments, the method comprises exposing the one or more items of medical or laboratory apparel and/or accessories to at least one disinfecting agent for at least 30 seconds, at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 15 minutes, at least 20 minutes, at least 25 minutes, at least 30 minutes, at least 1 hour, at least 2 hours, at least 3 hours, at least 4 hours, or at least 5 hours or more. In some embodiments, the method comprises exposing the one or more items of medical or laboratory apparel and/or accessories to at least one disinfecting agent for a time period of about 30 seconds to about 1 hour, about 30 seconds to about 30 minutes, about 30 seconds to about 25 minutes, about 30 seconds to about 20 minutes, about 30 seconds to about 15 minutes, about 30 seconds to about 10 minutes, about 1 minute to about 1 hour, about 1 minute to about 30 minutes, about 1 minute to about 15 minutes, about 5 minutes to about 1 hour, about 5 minutes to about 30 minutes, about 5 minutes to about 15 minutes, and the like.

In some embodiments, the method comprises exposing the one or more items of medical or laboratory apparel and/or accessories to the at least one disinfecting agent for a sufficient amount of time to inactivate or kill at least about 50%, 60%, 70%, 75%, 80%, 85%, 90%, 95%, 96%, 97%, 98%, 99% or 100% of the pathogens on the item of apparel and/or accessory. A person skilled in the art can readily determine the amount of time that is needed to inactivate or kill a certain percentage of pathogens on an item of apparel or accessory, for example, by collecting a sample from the item (e.g., a swab stick to a specific location on the item) prior to placing the item in the apparatus and after a certain period of exposure to the disinfecting agent in the apparatus, and inoculating the samples on appropriate media in petri dishes in order to identify and/or quantify the pathogens in each sample.

A person skilled in the art will recognize that for practicing the methods described herein, any apparatus as described herein can be used. The various embodiments of the cabinet, systems, processes and other components of the apparatus described in Sections II and III above and in Section V below are suitable for the use and practice of these methods.

V. Examples

The following examples are offered to illustrate, but not to limit the claimed invention.

Example 1

Disinfection Cabinet with UV Scanning Devices to Disinfect Hospital Uniforms

UV-C radiation can efficiently eliminate vegetative bacteria and is widely being used in hospitals. However, it has not been used to disinfect white coats that are used by health care workers, which tend to carry pathogenic bacteria, as shown by several studies.

The disinfection cabinet described herein is designed to focus on four main objectives: (1) maximize exposure of UV-C on the fabric or accessory surface; (2) hold multiple items of apparel and/or accessory; (3) ensure safety to users; and (4) gather usage statistics of the cabinet by each health care worker in order to send reminders to disinfect items of apparel and/or accessories at regular intervals. The basic design of the cabinet is illustrated in FIGS. 1A-C and FIGS. 2A-C.

The disinfection cabinet comprises the following components:

Scanning System:

The scanning system is the primary mechanical assembly within the cabinet. It has a slide (e.g., an XY linear slide) that can move a carriage to specified locations within the cabinet. This mechanical assembly is mounted on the back wall of the cabinet. The X-axis along which the carriage moves corresponds to horizontal motion and the Y-axis corresponds to vertical motion. The carriage holds the disinfection system and the uniform ID system. Two motors are used to provide motion for the two axes. The motors interface to the computer or PLC with a dedicated motor controller board. The motor rotation is translated to linear motion via a belt or gear driven interface or other mechanical means of providing the necessary motion of the scanner.

Disinfection System:

The disinfection system is a UV-C light source, either a mercury vapor lamp, a pulsed UV light, a monochromatic LED, or other sources in the UV-C wavelength range. This light source is mounted on the carriage of the scanning system described above. The scanning assembly, through systematic motion protocols, ensures maximum exposure of each item of apparel within the cabinet to UV-C light. In this design, each item of apparel is disinfected sequentially from one end of the cabinet to the other (or by means of some priority assignments). Optimal parameters for light intensity, distance to item of apparel, and rate of travel can be adjusted for the disinfection system.

Apparel and/or Accessory Identification System:

The apparel and/or accessories in the cabinet can be uniquely identified as belonging to a particular user (e.g., health care worker), such as by attaching a passive radio-frequency identification (RFID) tag to each item of apparel and/or accessory. When each item of apparel is being disinfected, its ID number is determined by means of an RFID reader mounted on the carriage of the scanning system. The combination of the RFID tag of each item and the time-stamp when it was disinfected will help in tracking the disinfection frequency of each item. If more than a certain duration of time (e.g., 24 hours) has passed since any item was last disinfected, an electronic message can be sent to the health care worker associated with that item of apparel and/or accessory.

LCD Touchscreen or User Interface Screen:

Health care workers can use a Graphic User Interface (GUI) on a touchscreen mounted on the door of the cabinet to unlock the cabinet to access their item(s) of apparel and/or accessories, determine the status of the disinfection cycle for their item(s), and determine the specific hanger within the cabinet where each item is located. All maintenance processes and administrative operations (e.g., adding users or uniform IDs) can also be handled through the GUI interface.

Electronic Lock:

A two-stage locking system can be incorporated for safety. In the two-stage locking system, an electronic lock keeps the cabinet doors shut. When a user wants to access the cabinet, he enters an electronic PIN number on the touchscreen or uses a digital key-card to unlock the cabinet door. Once an electronic signal is sent for the lock to open, another electronic signal is sent to ensure that the UV-C light source is turned off.

Software:

All the above systems are controlled by an embedded computer or a programmable logic controller (PLC) placed within the cabinet. The hardware communicates with the computer via input/output ports using software interrupt routines and drivers.

Example 2

Testing Results

Figure 3:
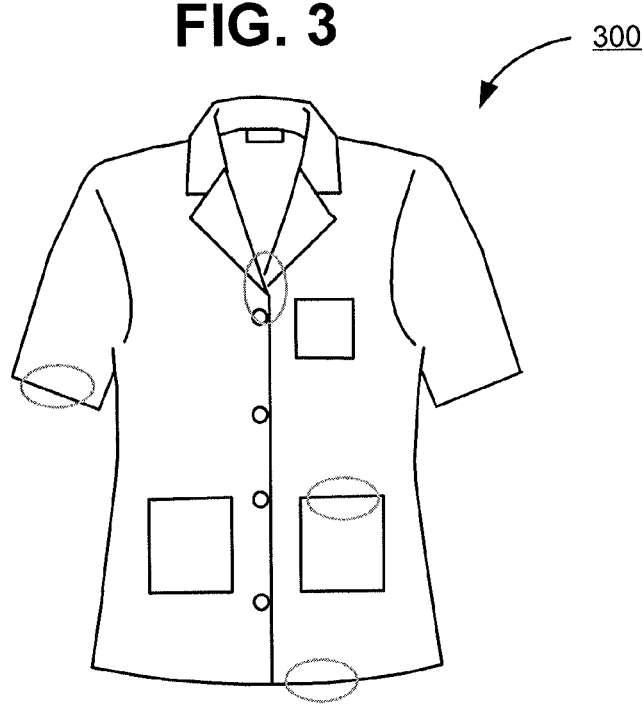
FIG. 3 is an illustration of a short sleeve coat and long sleeve coat.
Figure 3:
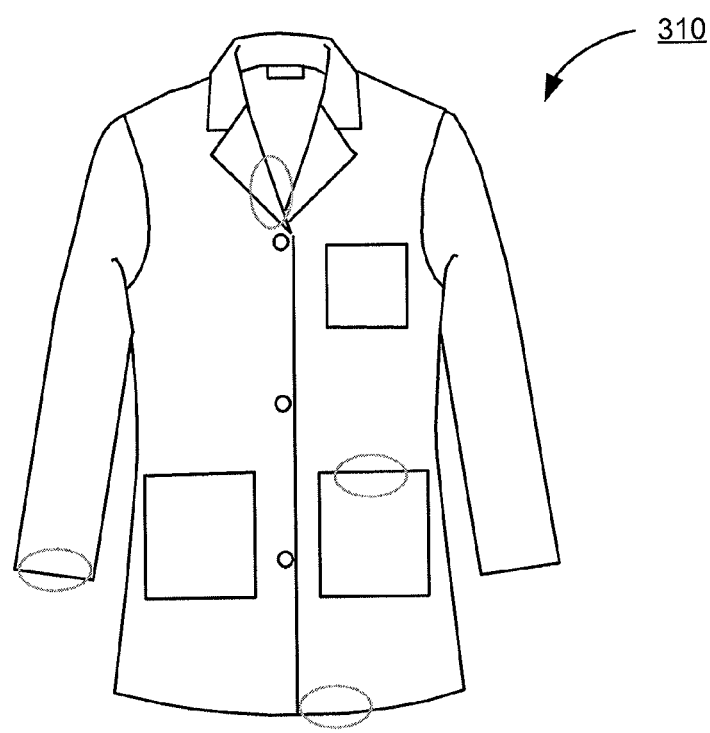

Methods:

The efficiency of the disinfection of the invention was measured by collecting bacterial samples from the white coats of physicians (both short sleeve and long sleeve coats). FIG. 3 illustrates the locations from which samples were collected as indicated by the circled regions on the coats (FIG. 3-300; 310). Samples were collected using standard procedures using swabs. Samples were grown on bacterial growth cultures under standard laboratory conditions by an accredited medical diagnostic laboratory. The culture plates were then incubated to observe bacterial growth. After 24 hours, the culture plates were analyzed to determine whether there was any bacterial growth. Tests were specifically performed to identify Gram positive bacilli, Gram negative bacilli and Gram positive cocci.

Observations:

Anywhere from 2-100 CFU (colony forming units) of bacteria (mentioned above) were isolated from several locations on coats before the disinfection process was performed (see Table 1, below). These infected coats were then disinfected in the apparatus described herein for anywhere from 1 minute to 10 minutes. A 100% disinfection was observed in most cases, while in a few cases, 1 CFU of bacteria was isolated after 10 minutes of disinfection (see Table 2, below), as shown by the culture studies post-disinfection in the apparatus described herein.

various modifications or changes in light thereof will be suggested to persons skilled in the art and are to be included within the spirit and purview of this application and scope of the appended claims. All publications, references, patents, and patent applications cited herein are hereby incorporated by reference in their entirety for all purposes.

VI. References

1. Scott R D (2009) The direct medical costs of Healthcare-Associated Infections in U.S. Hospitals and the benefits of prevention.
2. Prevention Cfdca (2010) Healthcare-associated Infections.
3. Allegranzi B (2011) Report on the burden of endemic healthcare-Associated infection worldwide. ed Sudan R (WHO).

TABLE 1

Infection Test

| Sample Location | Coat No. 1 | Coat No. 2 | Coat No. 3 |
|---|---|---|---|
| Right Hand Bottom Sleeves | 1. Gram positive cocci in clusters (4 CFU). 2. Gram positive bacilli (4 CFU). 3. Gram negative bacilli (2 CFU). | 1. Gram positive cocci in clusters (8 CFU). 2. Gram positive filamentous bacilli (3 CFU) 3. Budding yeast cells. | 1. Gram positive cocci in clusters (33 CFU). 2. Gram negative bacilli (4 CFU). |
| Top Right Near Chest | 1. Gram positive cocci in clusters (45 CFU). 2. Gram positive bacilli (4 CFU). | 1. Gram positive cocci in clusters (3 CFU). | 1. Gram positive cocci in clusters (22 CFU). 2. Gram negative bacilli (5 CFU) |
| Front Left Bottom Pocket | 1. Gram positive cocci in clusters (20 CFU). 2. Gram negative bacilli (3 CFU). | 1. Gram positive cocci in clusters (5 CFU). | 1. Gram positive cocci in clusters (52 CFU). 2. Gram negative bacilli (4 CFU). 3. Gram negative bacilli isolated (1 CFU). |
| Bottom Front Strip | 1. Gram positive cocci in clusters (15 CFU). 2. Gram positive bacilli (3 CFU). | 1. Gram positive cocci in clusters (10 CFU). 2. Gram positive bacilli (2 CFU). | 1. Gram positive cocci in clusters (60 CFU). 2. Gram negative bacilli (3 CFU). 3. Gram positive cocci in clusters isolated (1 CFU). |
| Most affected position | Top Right Near Chest | Right Hand Bottom Sleeves | Bottom Front Strip |

TABLE 2

Disinfection Test

| Sample Location | Coat No. 1 | Coat No. 2 | Coat No. 3 |
|---|---|---|---|
| Right Hand Bottom Sleeves | No organism isolated. | No organism isolated. | No organism isolated. |
| Top Right Near Chest | No organism isolated. | No organism isolated. | No organism isolated. |
| Front Left Bottom Pocket | No organism isolated. | No organism isolated. | Gram negative bacilli isolated (1 CFU). |
| Bottom Front Strip | No organism isolated. | No organism isolated. | Gram positive cocci in clusters isolated (1 CFU). |
| Most Disinfected Position | All | All | Right Hand Bottom Sleeves; Top Right Near Chest |

It is understood that the examples and embodiments described herein are for illustrative purposes only and that 4. Frieden T R (2010) Maximizing infection prevention in the next decade: Defining the unacceptable. *Infection control and hospital epidemiology* 30(S1): S1-S3.
5. Wiener-Well Y, et al. (2011) Nursing and physician attire as possible source of nosocomial infections. *American journal of infection control* 39(7):555-559.
6. Gaspard P, et al. (2009) Meticillin-resistant *Staphylococcus aureus* contamination of healthcare workers' uniforms in long-term care facilities. *The Journal of hospital infection* 71(2):170-175.
7. Nordstrom J M, Reynolds K A, & Gerba C P (2012) Comparison of bacteria on new, disposable, laundered, and unlaundered hospital scrubs. *American journal of infection control* 40(6):539-543.
8. Hambraeus A (1973) Transfer of *Staphylococcus aureus* via nurses' uniforms. *The Journal of hygiene* 71(4):799-814.
9. Hambraeus A (1973) Dispersal and transfer of *Staphylococcus aureus* in an isolation ward for burned patients. *The Journal of hygiene* 71(4):787-797.

10. Hambraeus A & Laurell G (1973) Infections in a burns unit. An attempt to study the airborne transfer of bacteria. *Contributions to microbiology and immunology* 1:459-468.
11. Speers R, Jr., Shooter R A, Gaya H, & Patel N (1969) Contamination of nurses' uniforms with *Staphylococcus aureus*. *Lancet* 2(7614):233-235.
12. Lidwell O M, Towers A G, Ballard J, & Gladstone B (1974) Transfer of microorganisms between nurses and patients in a clean air environment. *The Journal of applied bacteriology* 37(4):649-656.
13. Hambraeus A & Ransjo U (1977) Attempts to control clothes-borne infection in a burn unit. I. Experimental investigations of some clothes for barrier nursing. *The Journal of hygiene* 79(2):193-202.
14. Ransjo U (1979) Attempts to control clothes-borne infection in a burn unit, 3. An open-roofed plastic isolator or plastic aprons to prevent contact transfer of bacteria. *The Journal of hygiene* 82(3):385-395.
15. Ransjo U (1979) Attempts to control clothes-borne infection in a burn unit, 2. Clothing routines in clinical use and the epidemiology of cross-colonization. *The Journal of hygiene* 82(3):369-384.
16. Nystrom B (1981) The contamination of gowns in an intensive care unit. *The Journal of hospital infection* 2(2):167-170.
17. Loh W, Ng V V, & Holton J (2000) Bacterial flora on the white coats of medical students. *The Journal of hospital infection* 45(1):65-68.
18. Uneke C J & Ijeoma P A (2010) The potential for nosocomial infection transmission by white coats used by physicians in Nigeria: implications for improved patient-safety initiatives. *World health &population* 11(3):44-54.
19. Munoz-Price L S, et al. (2012) Associations between bacterial contamination of health care workers' hands and contamination of white coats and scrubs. *American journal of infection control* 40(9):E245-E248.
20. Burden M, et al. (2011) Newly Cleaned Physician Uniforms and Infrequently Washed White Coats Have Similar Rates of Bacterial Contamination After an 8-Hour Workday: A Randomized Controlled Trial. *J Hosp Med* 6(4):177-182.
21. Treakle A M, et al. (2009) Bacterial contamination of health care workers' white coats. *American journal of infection control* 37(2): 101-105.
22. Klein B S, Perloff W H, & Maki D G (1989) Reduction of nosocomial infection during pediatric intensive care by protective isolation. *N Engl J Med* 320(26):1714-1721.
23. Peleg A Y & Hooper D C (2010) Hospital-acquired infections due to gram-negative bacteria. *N Engl J Med* 362(19): 1804-1813.
24. Kallen J Alexander J T J, Laxminarayanan Ramanan, Ricks Philip (2013) Vital Signs: Carbapenem-Resistant Enterobacteriaceae. (Centers for disease control and prevention), pp 165-170.
25. B. vdwM (2001) White coats and the medical profession: Time to rediscover the symbol of our purpose and our pride? *Medical journal of Australia* 174:324-325.
26. Hijnen W A, Beerendonk E F, & Medema G J (2006) Inactivation credit of UV radiation for viruses, bacteria and protozoan (oo)cysts in water: a review. *Water research* 40(1):3-22.
27. Becker M M & Wang Z (1989) Origin of Ultraviolet Damage in DNA. *J Mol Biol* 210(3):429-438.
28. Conner-Kerr T A, Sullivan P K, Gaillard J, Franklin M E, & Jones R M (1998) The effects of ultraviolet radiation on antibiotic-resistant bacteria in vitro. *Ostomy/wound management* 44(10):50-56.
29. Nerandzic M M, Cadnum J L, Pultz M J, & Donskey C J (2010) Evaluation of an automated ultraviolet radiation device for decontamination of *Clostridium difficile* and other healthcare-associated pathogens in hospital rooms. *BMC infectious diseases* 10:197.
30. Allegranzi B, et al. (2011) Burden of endemic health-care-associated infection in developing countries: systematic review and meta-analysis. *Lancet* 377(9761):228-241.
31. Burwen D R, et al. (2001) Invasive aspergillosis outbreak on a hematology-oncology ward. *Infection control and hospital epidemiology* 22(1):45-48.
32. Perfect J R & Schell W A (1996) The new fungal opportunists are coming. *Clin Infect Dis* 22:S112-S118.
33. Solomon S L, et al. (1986) Nosocomial Fungemia in Neonates Associated with Intravascular Pressure-Monitoring Devices. *Pediatr Infect Dis J* 5(6):680-685.
34. Denning D W (1998) Invasive aspergillosis. *Clin Infect Dis* 26(4):781-803.
35. Kao A S, et al. (1999) The epidemiology of candidemia in two United States cities: Results of a population-based active surveillance. *Clin Infect Dis* 29(5):1164-1170.
36. Services USDoHH (2012) National Action Plan to Prevent Healthcare-Associated Infections: Roadmap to Elimination.
37. CDC (2012) CDC-Winnable Battles-Healthcare-associated Infections. (Centers for Disease Control and Prevention).
38. Sehulster LCYWR (2003) Guidelines for Environmental Infection Control in Health-Care Facilities. (U.S. Department of Health and Human Services; Centers for Disease Control and Prevention (CDC), Atlanta).
39. Palazzo S & Hocken D B (2010) Patients' perspectives on how doctors dress. *The Journal of hospital infection* 74(1):30-34.
40. Barrie D (1994) Infection-Control in Practice—How Hospital Linen and Laundry Services Are Provided. *Journal of Hospital Infection* 27(3):219-235.
41. Anonymous (1981) *Laundry Additives-Residual Self-Sanitization*, (Agency USEp).
42. Perry C, Marshall R, & Jones E (2001) Bacterial contamination of uniforms. *The Journal of hospital infection* 48(3):238-241.
43. Pilonetto M, et al. (2004) Hospital gowns as a vehicle for bacterial dissemination in an intensive care unit. The Brazilian journal of infectious diseases: an official publication of the *Brazilian Society of Infectious Diseases* 8(3):206-210.
44. Saloojee H & Steenhoff A (2001) The health professional's role in preventing nosocomial infections. *Postgraduate medical journal* 77(903): 16-19.
45. Jason K (2013) Beagleboard.org.
46. Bob V (2003) Genesis of the versatile RFID tag.
47. al WNJe (1952) USPTO 2,612,994.
48. Davies A, Pottage T, Bennett A, & Walker J (2011) Gaseous and air decontamination technologies for *Clostridium difficile* in the healthcare environment. *J Hosp Infect* 77(3):199-203.
49. Moore G, et al. (2012) Use of UV-C radiation to disinfect non-critical patient care items: a laboratory assessment of the Nanoclave Cabinet. *BMC Infect Dis* 12:174.
50. Pigeot-Remy S, Simonet F, Atlan D, Lazzaroni J C, & Guillard C (2012) Bactericidal efficiency and mode of action: A comparative study of photochemistry and photocatalysis. *Water research* 46(10):3208-3218.

51. Moore G, et al. (2012) Use of UV-C radiation to disinfect non-critical patient care items: a laboratory assessment of the Nanoclave Cabinet. *BMC infectious diseases* 12.

What is claimed is:

1. A method for disinfecting one or more items of medical or laboratory apparel or accessories, the method comprising:
   placing the one or more items in an apparatus comprising (i) a cabinet; (ii) a disinfecting system housed within the cabinet, wherein the disinfecting system comprises at least one disinfecting agent; (iii) a scanning system housed within the cabinet, wherein the scanning system comprises a slide and a carriage mounted on the slide; and (iv) an embedded computer or a programmable logic controller housed within the cabinet; and
   exposing the one or more items to the disinfecting agent under conditions suitable for inactivating or killing pathogens, thereby disinfecting or sterilizing the one or more items.

2. The method of claim 1, wherein the one or more items of apparel is selected from the group consisting of coats, scrubs, uniforms, aprons, shoes, and combinations thereof.

3. The method of claim 2, wherein the coats are white coats, lab coats, or combinations thereof.

4. The method of claim 1, wherein the one or more items of accessories is selected from the group consisting of shoes, socks, ties, hosiery, watches, headbands, scrub caps, stethoscopes, mobile phones, note pads, writing equipment, pressure cuffs, and combinations thereof.

5. The method of claim 1, wherein the disinfecting agent is selected from the group consisting of: a source of ultraviolet radiation, a source of infrared light, a chemical, and any combination thereof.

6. The method of claim 5, wherein the source of ultraviolet radiation is selected from the group consisting of an ultraviolet mercury vapor lamp, an ultraviolet light-emitting diode, a pulsed ultraviolet lamp, an ultraviolet deuterium lamp, an ultraviolet metal halide lamp, and other UV light emitting sources.

7. The method of claim 1, further comprising exposing the one or more items to one or more disinfection cycles.

8. The method of claim 1, further comprising exposing the one or more items to the disinfecting agent for a time period of about 30 seconds to about 1 hour.

9. The method of claim 1, wherein the embedded computer or programmable logic controller controls the disinfection system.

10. The method of claim 9, wherein the embedded computer or programmable logic controller further controls one or more systems selected from the group consisting of the scanning system, a horizontal linear sub-system, a vertical linear sub-system, a garment identification system, a hanging system, a hanger state measurement system, an access device, a human machine interface, a lighting system, a locking system, a calibration system, and a ranging system.

11. The method of claim 1, wherein the apparatus further comprises a hanger system housed within the cabinet.

12. The method of claim 11, wherein the hanger system comprises one or more hangers configured in either fixed positions or dynamic positions.

13. The method of claim 1, wherein the apparatus further comprises a garment identification system.

14. The method of claim 1, wherein the apparatus further comprises a display screen mounted to the exterior of the cabinet.

15. The method of claim 1, wherein the cabinet comprises one or more interior surfaces coated with a reflective material.

16. The method of claim 1, further comprising sending an electronic message to a user of the apparatus.

17. The method of claim 16, wherein the message is selected from a group consisting of a reminder to disinfect one or more of the one or more items, a status of the one or more items, a status of a disinfection cycle, and any combination thereof.

18. The method of claim 16, wherein sending an electronic message to a user of the apparatus further comprises sending the electronic message at pre-determined intervals of time.

* * * * *